United States Patent
Manku et al.

(10) Patent No.: US 8,617,594 B2
(45) Date of Patent: *Dec. 31, 2013

(54) STABLE PHARMACEUTICAL COMPOSITION AND METHODS OF USING SAME

(71) Applicant: Amarin Pharmaceuticals Ireland Limited, Dublin (IE)

(72) Inventors: Mehar Manku, England (GB); Ian Osterloh, Kent (GB); Pierre Wicker, Mystic, CT (US); Rene Braeckman, Richboro, PA (US); Paresh Soni, Mystic, CT (US)

(73) Assignee: Amarin Pharmaceuticals Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/777,412

(22) Filed: Feb. 26, 2013

(65) Prior Publication Data
US 2013/0171251 A1 Jul. 4, 2013

Related U.S. Application Data

(63) Continuation of application No. 13/685,291, filed on Nov. 26, 2012, which is a continuation of application No. 13/614,111, filed on Sep. 13, 2012, now Pat. No. 8,454,994, which is a continuation of application No. 13/458,496, filed on Apr. 27, 2012, now Pat. No. 8,445,003, which is a continuation of application No. 12/769,885, filed on Apr. 29, 2010, now Pat. No. 8,298,554.

(60) Provisional application No. 61/173,763, filed on Apr. 29, 2009.

(51) Int. Cl.
*A61K 9/48* (2006.01)
*A61K 31/232* (2006.01)
*A61K 31/202* (2006.01)
*A61P 9/00* (2006.01)
*A61P 9/10* (2006.01)

(52) U.S. Cl.
USPC ........... 424/456; 424/400; 424/451; 514/549; 514/560

(58) Field of Classification Search
USPC .................. 424/456, 400, 451; 514/549, 560
See application file for complete search history.

(56) References Cited

U.S. PATENT DOCUMENTS

| | | | |
|---|---|---|---|
| 4,377,526 | A | 3/1983 | Fujita et al. |
| 4,526,902 | A | 7/1985 | Rubin |

(Continued)

FOREIGN PATENT DOCUMENTS

| | | |
|---|---|---|
| CA | 2628305 | 5/2007 |
| CA | 2653787 | 12/2007 |

(Continued)

OTHER PUBLICATIONS

Aarsland, et al., "On the Effect of Peroximsomal β-Oxidation and Carnitine Palmitoyltransferase Activity by Eicosapentaenoic Aid in Live and Heart of Rats." Lipids, 25:546-548, (1990).

(Continued)

*Primary Examiner* — Aradhana Sasan
(74) *Attorney, Agent, or Firm* — Perkins Coie LLP

(57) ABSTRACT

The present invention relates to, inter alia, pharmaceutical compositions comprising a polyunsaturated fatty acid and to methods of using the same to treat or prevent cardiovascular-related diseases.

26 Claims, 2 Drawing Sheets

(56) References Cited

U.S. PATENT DOCUMENTS

| | | | |
|---|---|---|---|
| 4,920,098 A | 4/1990 | Cotter et al. | |
| 4,935,243 A | 6/1990 | Borkan et al. | |
| 5,013,443 A | 5/1991 | Higashidate et al. | |
| 5,116,871 A | 5/1992 | Horrobin et al. | |
| 5,178,873 A | 1/1993 | Horrobin et al. | |
| 5,198,468 A | 3/1993 | Horrobin | |
| 5,215,630 A | 6/1993 | Hata et al. | |
| 5,252,333 A | 10/1993 | Horrobin | |
| 5,343,389 A * | 8/1994 | Otvos | 436/173 |
| 5,457,130 A | 10/1995 | Tisdale et al. | |
| 5,502,077 A | 3/1996 | Breivik et al. | |
| 5,567,730 A | 10/1996 | Miyashita et al. | |
| 5,589,508 A | 12/1996 | Schlotzer et al. | |
| 5,603,959 A | 2/1997 | Horrobin et al. | |
| 5,618,558 A | 4/1997 | Horrobin et al. | |
| 5,656,667 A | 8/1997 | Breivik et al. | |
| 5,698,594 A | 12/1997 | Breivik et al. | |
| 5,760,081 A | 6/1998 | Leaf et al. | |
| 5,776,978 A | 7/1998 | Bruzzese | |
| 5,837,731 A | 11/1998 | Vaddadi | |
| 5,840,944 A | 11/1998 | Furihata et al. | |
| 5,888,541 A | 3/1999 | Horrobin et al. | |
| 6,069,168 A | 5/2000 | Horrobin et al. | |
| 6,193,999 B1 | 2/2001 | Gennadios | |
| 6,326,031 B1 | 12/2001 | Hsia et al. | |
| 6,331,568 B1 | 12/2001 | Horrobin | |
| 6,368,621 B1 | 4/2002 | Engel et al. | |
| 6,384,077 B1 | 5/2002 | Peet et al. | |
| 6,479,544 B1 | 11/2002 | Horrobin | |
| 6,531,150 B1 | 3/2003 | Sunohara et al. | |
| 6,555,700 B1 | 4/2003 | Horrobin et al. | |
| 6,689,812 B2 | 2/2004 | Peet | |
| 7,119,118 B2 | 10/2006 | Peet | |
| 7,498,359 B2 | 3/2009 | Yokoyama et al. | |
| 8,188,146 B2 | 5/2012 | Peet et al. | |
| 8,293,727 B2 | 10/2012 | Manku et al. | |
| 8,293,728 B2 | 10/2012 | Manku et al. | |
| 8,298,554 B2 | 10/2012 | Manku | |
| 8,314,086 B2 | 11/2012 | Manku et al. | |
| 8,318,715 B2 | 11/2012 | Manku et al. | |
| 8,324,195 B2 | 12/2012 | Manku et al. | |
| 8,357,677 B1 | 1/2013 | Manku et al. | |
| 8,367,652 B2 | 2/2013 | Manku et al. | |
| 8,377,920 B2 | 2/2013 | Manku et al. | |
| 2002/0016312 A1 | 2/2002 | Seed et al. | |
| 2002/0035125 A1 | 3/2002 | Shear | |
| 2002/0055529 A1 | 5/2002 | Bisgaier et al. | |
| 2002/0055539 A1 | 5/2002 | Bockow et al. | |
| 2002/0077361 A1 | 6/2002 | Peet | |
| 2002/0183389 A1 | 12/2002 | Peet | |
| 2002/0193439 A1 | 12/2002 | Peet | |
| 2002/0198177 A1 | 12/2002 | Horrobin et al. | |
| 2003/0100610 A1 | 5/2003 | Shibuya et al. | |
| 2003/0104048 A1 | 6/2003 | Patel et al. | |
| 2003/0166614 A1 | 9/2003 | Harrison, Jr. | |
| 2004/0077723 A1 | 4/2004 | Granata | |
| 2004/0162348 A1 | 8/2004 | Peet | |
| 2005/0187292 A1 | 8/2005 | Aoki et al. | |
| 2006/0034815 A1 | 2/2006 | Guzman et al. | |
| 2006/0134178 A1 | 6/2006 | Doisaki et al. | |
| 2006/0135610 A1 | 6/2006 | Bortz et al. | |
| 2006/0141022 A1 | 6/2006 | Kawamura et al. | |
| 2006/0142390 A1 | 6/2006 | Manku et al. | |
| 2006/0211762 A1 | 9/2006 | Rongen | |
| 2006/0211763 A1 | 9/2006 | Fawzy et al. | |
| 2006/0217356 A1 | 9/2006 | Wright et al. | |
| 2006/0252833 A1 | 11/2006 | Peet | |
| 2007/0104779 A1 | 5/2007 | Rongen et al. | |
| 2007/0105954 A1 | 5/2007 | Puri | |
| 2007/0141138 A1 | 6/2007 | Feuerstein et al. | |
| 2007/0167520 A1 | 7/2007 | Bruzzese | |
| 2007/0191467 A1 | 8/2007 | Rongen et al. | |
| 2008/0020018 A1 | 1/2008 | Moodley et al. | |
| 2008/0089876 A1 | 4/2008 | Cavazza | |
| 2008/0113046 A1 | 5/2008 | Gardette | |
| 2008/0125490 A1 | 5/2008 | Svensson et al. | |
| 2008/0200547 A1 | 8/2008 | Peet et al. | |
| 2008/0306154 A1 | 12/2008 | Svensson et al. | |
| 2008/0319077 A1 | 12/2008 | Suzuki et al. | |
| 2009/0012167 A1 | 1/2009 | Rongen et al. | |
| 2009/0182049 A1 | 7/2009 | Opheim | |
| 2009/0227602 A1 | 9/2009 | Griffin et al. | |
| 2009/0304784 A1 | 12/2009 | Mane et al. | |
| 2010/0021555 A1 | 1/2010 | Geiringer et al. | |
| 2010/0119598 A1 | 5/2010 | Yoshinari et al. | |
| 2010/0311834 A1 | 12/2010 | Manku et al. | |
| 2011/0034555 A1 | 2/2011 | Osterloh et al. | |
| 2011/0288171 A1 | 11/2011 | Manku et al. | |
| 2012/0100208 A1 | 4/2012 | Manku | |

FOREIGN PATENT DOCUMENTS

| | | |
|---|---|---|
| CA | 2675836 | 7/2008 |
| CA | 2724983 | 11/2009 |
| EP | 0302482 | 2/1989 |
| EP | 0460917 | 12/1991 |
| EP | 0606012 | 7/1994 |
| EP | 0610506 | 8/1994 |
| EP | 1157692 | 11/2001 |
| EP | 1296670 | 4/2003 |
| EP | 1743644 | 1/2007 |
| EP | 2022495 | 2/2009 |
| FR | 2635263 | 2/2009 |
| GB | 2148713 | 6/1985 |
| GB | 2221843 | 2/1990 |
| GB | 2229363 | 9/1990 |
| GB | 9901809.5 | 1/1999 |
| HU | P0200686 | 8/1990 |
| JP | 04182426 | 6/1992 |
| KR | 10-2006-0109988 | 10/2006 |
| WO | WO 90/04391 | 5/1990 |
| WO | WO 92/21335 | 12/1992 |
| WO | WO 94/28891 | 12/1994 |
| WO | WO 97/39759 | 10/1997 |
| WO | WO 98/16216 | 4/1998 |
| WO | WO 99/29316 | 6/1999 |
| WO | WO 00/44361 | 8/2000 |
| WO | WO 00/51573 | 9/2000 |
| WO | WO 01/15552 | 3/2001 |
| WO | WO 02/02105 | 1/2002 |
| WO | WO 02/058793 | 8/2002 |
| WO | WO 02/089787 | 11/2002 |
| WO | WO 02/096408 | 12/2002 |
| WO | WO 03/068216 | 8/2003 |
| WO | WO 2004/050913 | 6/2004 |
| WO | WO 2004/078166 | 9/2004 |
| WO | WO 2004/082402 | 9/2004 |
| WO | WO 2007/016256 | 2/2007 |
| WO | WO 2007/017240 | 2/2007 |
| WO | WO 2007/073176 | 6/2007 |
| WO | WO 2007/075841 | 7/2007 |
| WO | WO 2007/128801 | 11/2007 |
| WO | WO 2007/142118 | 12/2007 |
| WO | WO 2008/004900 | 1/2008 |
| WO | WO 2008/045465 | 4/2008 |
| WO | WO 2008/106787 | 9/2008 |
| WO | WO 2009/004999 | 1/2009 |

OTHER PUBLICATIONS

Aas, V., et al., "Eicosapentaenoic acid (20:5 n-3) increases fatty acid and glucose uptake in cultured human skeletal muscle cells." Journal of Lipid Research, 47:366-374 (2006).

Abbey, M., et al., "Effect of fish oil on lipoproteins, lecithin:cholesterol acyltransferase, and lipidtransfer protein activity in humans" Arterioscler. Thromb. Vasc. Biol. 10:85-94 (1990).

Ackman et al., The "Basic" Fatty Acid Composition of Atlantic Fish Oils: Potential Similarties Useful for Enrichment of Polyunsaturated Fatty Acids by Urea Complexation, JAOCS, vol. 65, 1:136-138 (Jan. 1988).

Adan, Y., et al., "Effects of docosahexaenoic and eicosapentaenoic acid on lipid metabolism, eicosanoid production, platelet aggregation

(56) References Cited

OTHER PUBLICATIONS and atherosclerosis." Biosci. Biotechnol. Biochem. 63(1), 111-119 (1999).
Adan, Y., et al., "Concentration of serum lipids and aortic lesion size in female and male apo E-deficient mice fed docosahexaenoic acid." Biosci. Biotechnol. Biochem. 63(2):309-313 (1999).
Agren, J.J., et al., "Fatty acid composition of erythrocyte, platelet, and serum lipids in strict vegans." Lipids 30:365-369 (1995).
Agren, J.J., et al., "Fish diet, fish oil and docosahexaenoic acid rich oil lower fasting and postprandial plasma lipid levels." Eur J Clin Nutr. 1996;50:765-771.
Ando, M., et al., "Eicosapentanoic acid reduces plasma levels of remnant lipoproteins and prevents in vivo peroxidation of LDL in dialysis patients." J. Am. Soc. Nephrol., 10:2177-2184 (1999).
Ando, Y., et al., "Positional distribution of highly unsaturated fatty acids in triacyl-sn-glycerols of Artemia Nauplii enriched with docosahexaenoic acid ethyl ester." Lipids 36:733-740 (2001).
Andrade, S.E., et al., (1995) Discontinuation of antihyperlipidaemic drugs_do rates reported in clinical trials reflect rates in primary care settings? New Eng. J. Med. 332: 1125-1131.
Angerer, P., et al., "n-3 Polyunsaturated Fatty Acids and the Cardiovascular System", Current Opinion in Lipidology, 11(1):57-63, 2000.
Anil, E., "The Impact of EPA and DHA on Blood Lipids and Lipoprotein Metabolism: Influence of ApoE Genoty[e", Proceedings of the Nutrition Society, 66:60-68, 2007.
Appelton, K.M., et al., "Effects of n-3 long-chain polyunsaturated fatty acids on depressed mood: systematic review of published trials," Am. J. Clin. Nutr. 84(6):1308-1316 (Dec. 2006).
Arrol, S. et al., "The effects of fatty acids on apolipoprotein B secretion by human hepatoma cells (HEP G2)," Atherosclerosis 150 (2000) 255-264.
Arshad, A., et al., "Sudden cardiac death and the role of medical therapy." Progress in Cardiovascular Diseases, vol. 50, No. 6, 420-438, (2008).
Arterburn, L., et al., "Distribution, interconversion, and dose response of n-3 fatty acids in humans." Am J Clin Nutr., 83:1467S-76S (2006).
Asano, M., et al., "Eicosapentaenoic acid inhibits vasopressin-activated Ca2q influx and cell proliferation in rat aortic smooth muscle cell lines." European Journal of Pharmacology 379:199-209 (1999).
Asano, M., et al., "Inhibitory effects of ω-3 polyunsaturated fatty acids on receptor-mediated non-selective cation currents in rat A7r5 vascular smooth muscle cells." British Journal of Pharmacology 120:1367-1375, (1997).
ATP III guidelines, NIH publication No. 01-3305 (2001).
Ayton, et al., "A pilot open case series of Ethyl-EPA supplementation in the treatment of anorexia nervosa," Prostaglandins, Leukotrienes and Essential Fatty Acids 71 (2004) pp. 205-209.
Ayton, et al., "Rapid improvement of severe anorexia nervosa during treatment with ethyl-eicosapentaenoate and micronutrients," European Psychiatry 19 (2004) pp. 317-319.
Baigent, C., et al., "Efficacy and safety of cholesterol-lowering treatment: prospective meta-analysis of data from 90,056 participants in 14 randomised trials of statins." Lancet. 2005;366:1267-1278.
Balk, E.M., et al., "Effects of omega-3 fatty acids on serum markers of cardiovascular disease risk: a systematic review. Atherosclerosis." 2006;189:19-30.
Ballantyne et al., Influence of low-high density lipoprotein cholesterol and elevated triglyceride on coronary heart disease events and response to simvastatin therapy in 4S, Circulation 2001, 104:3046-3051.
Bang Ho, Dyerberg J. "Plasma lipids and Lipoproteins in Greenlandic west coast Eskimos" Acta Med Scand 1972; 192:85-94.
Banga, A., et al., "Adiponectin translation is increased by the PPARγ agonists pioglitazone and ω-3 fatty acids." Am J Physiol Endocrinal Metab 296:480-489 (2009).
Bansal S, Buring JE, Rifai N, Mora S, Sacks FM, Ridker PM, "Fasting Compared With Nonfasting Triglycerides and Risk of Cardiovascular Events in Women," JAMA 2007; 298:309-316.

Basu, A., et al., "Dietary Factors That Promote or Retard Inflammation." Arterioscler. Thromb. Vasc. Biol. 26:995-1001 (2006).
Bays He et al. "Prescription omega-3 fatty acids and their lipid effects: physiologic mechanisms of action and clinical implications," Expert Rev Cardiovasc Ther 2008; 6:391-409.
Bays, H., Clinical Overview of Omacor: A Concentrated Formulation of Omega-3 Polyunsaturated Fatty Acids, Am J cardiol 2006;98[suppl]:71i-76i.
Bays, H., "Rationale for Prescription Omega-3-Acid Ethyl Ester Therapy for Hypertriglyceridemia: A Primer for Clinicians," Drugs of Today 2008,44(3); 205-246.
Bays, H.E., et al., "Long-term up to 24-month efficacy and safety of concomitant prescription omega-3-acid ethyl esters and simvastatin in hypertriglyceridemic patients." Curr Med Res Opin. 2010;26:907-915.
Bays, H.E., Eicosapentaenoic Acid Ethyl Ester (AMR101) Therapy in Patients With Very High Triglyceride Levels (from the Multicenter, plAcebo-controlled, Randomized, double-bIINd, 12-week study with an open-label Extension [MARINE] Trial) Am J Cardiol 2011;108:682-690.
Beal, M.F., Annals of Neurology, vol. 38, No. 3, "Aging, Energy, and Oxidative Stress in Neurodegenerative Diseases", pp. 357-366, Sep. 1995.
Belmaker, et al., "Addition of Omega-3 Fatty Acid to Maintenance Medication Treatment for Recurrent Unipolar Depressive Disorder," Am J Psychiatry 2002; 159:477-479.
Belmaker, et al., "Omega-3 Eicosapentaenoic Acid in Bipolar Depression: Report of a Small Open-Label Study," J Clin Psychiatry 2005 66:726-729.
Bénistant, C., et al., "Docosapentaenoic acid (22:5, n-3): metabolism and effect on prostacyclin production in endothelial cells." Prostaglandins, Leukotrienes and Essential Fatty Acids, 55(4):287-292, (1996).
Berge, R.K., et al., "In contrast with docosahexaenoic acid, eicosapentaenoic acid and hypolipidaemic derivatives decrease hepatic synthesis and secretion of triacylglycerol by decreased diacylglycerol acyltransferase activity and stimulation of fatty acid oxidation." Biochem J. 1999; 343(Pt 1):191-197.
Betteridge, D.J., "Diabetic dyslipidaemia: past, present and future." Practical Diabetes Int, 21(2): 78-85. (2004).
Black, K.L., et al., "Effect of intravenous eicosapentaenoic acid on cerebral blood flow, edema, and brain prostaglandins in ischemic gerbils", Prostaglandins (1984), 28(4), pp. 545-546.
Blankenhorn, D.H., et al., (1987) Beneficial effects of combined colestipol-naicin therapy on coronary atheroscherosis and coronary venous bypass grafts. JAMA 257: 3233-3240.
Block, R. C., et al., "EPA and DHA in blood cell membranes from acute coronary syndrome patients and controls." Atherosclerosis, 197(2):821-828 (2007).
Blumenthal (Advanced Studies in Medicine (2002) 2:148-157).
Bonaa, KH et al., Docosahexaenoic and Eicosapentaenoic acids in plasma phospholipids are divergently associated with high density lipoprotein in humans, Arterioscler. Thromb. Vasc. Biol. 1992;12;675-681.
Bousserouel, S., et al., "Different effects of n-6 and n-3 polyunsaturated fatty acids on the activation of rat smooth muscle cells by interleukin-1β." J. Lipid Res. 44:601-611 (2003).
Bousserouel, S., et al., "Modulation of cyclin D1 and early growth response factor-1 gene expression in interleukin-1β-treated rat smooth muscle cells by n-6 and n-3 polyunsaturated fatty acids." Eur. J. Biochem. 271:4462-4473 (2004).
Brady, L., et al., Increased n-6 polyunsaturated fatty acids do not attenuate the effects of long-chain n-3 polyunsaturated fatty acids on insulin sensitivity or triacylglycerol reduction in Indian Asians. Am J Clin Nutr 79:983-91(2004).
Breslow, J., "n-3 Fatty acids and cardiovascular disease." Am J Clin Nutr., 83:1477S-82S (2006).
Brossard, N., et al., "Retroconversion and metabolism of [13C]22:6n-3 in humans and rats after intake of a single dose of [13C]22:6n-3-3-triacyylglycerols." Am. J. Clin. Nutr. 64:577-86 (1996).

(56) References Cited

OTHER PUBLICATIONS

Brouwer, I.A., et al., "Effect of fish oil on ventricular tachyarrhythmia and death in patients with implantable cardioverter defibrillators." JAMA. 295(22):2613-2619 (2006).
Brown et al., Simvastatin and Niacin, Antioxidant Vitamins, or the Combination for the Prevention of Coronary Disease, N Engl J Med, vol. 345, No. 22, Nov. 29, 2001.
Brown, A. J., et al., "Administration of n-3 Fatty Acids in the Diets of Rats or Directly to Hepatocyte Cultures Results in Different Effects on Hepatocellular ApoB Metabolism and Secretion." Arterioscler. Thromb. Vasc. Biol. 19:106-114 (1999).
Brown, A. J., et al., "Persistent changes in the fatty acid composition of erythrocyte membranes after moderate intake of n-3 polyunsaturated fatty acids: study design and implications." Am.J. Clin. Nutri. 54:668-73(1991).
Brown, G., et al., (1990) Regression of coronary artery-disease as a result of intensive lipid-lowering therapy in men with high levels of apolipoprotein B., N. Engl. J. Med. 323: 1289-1298.
Bryhn, M., et al., "The bioavailability and pharmacodynamics of different concentrations of omega-3 acid ethyl esters." Prostaglandins, Leukotrienes and Essential Fatty Acids 75:19-24 (2006).
Budavari, S., Editor, The Merck Index, 1989, Merck & Co., Inc., Rahway, N.J., entry 2417 on p. 379 and 4511 on p. 725.
Bunting, et al., "Depression in Parkinson's Disease", J. Neurosci Nurs. Jun. 1991; 23(3):158-164, (Abstract Only).
Burdge, G.C., et al., "Eicosapentaenoic and docosapentaenoic acids are the principal products of a-linolenic acid metabolism in young men." British Journal of Nutrition 88:355-363 (2002).
Burdge, G.C., et al., "Lack of effect of meal fatty acid composition on postprandial lipid, glucose and insulin responses in men and women aged 50-65 years consuming their habitual diets." British Journal of Nutrition, 96:489-500 (2006).
Burdge, G.C., et al., "The effect of altering the 20:5n-3 and 22:6n-3 content of a meal on the postprandial incorporation of n-3 polyunsaturated fatty acids into plasma triacylglycerol and non-esterified fatty acids in humans." Prostaglandins, Leukotrienes and Essential Fatty Acids 77:59-65 (2007).
Burr, M. L., et al., "Effects of changes in fat, fish and fibre intakes on death and myocardial reinfarction: Diet and reinfarction trial." The Lancet, Sep. 30, 1989; 2(8666):757-61.
Calabresi, L., et al., "Omacor in familial combined hyperlipidemia: effects on lipids and low density lipoprotein subclasses." Atherosclerosis 148:387-396 (2000).
Campos, H., et al., "Lowdensity lipoprotein size, pravastatin treatment, and coronary events." JAMA. 2001;286:1468-1474.
Canner, P.L., et al., (1986) Fifteen year mortality in Coronary Drug Project patients: long-term benefit with niacin, J. Am. Coll. Cardiol. 8. 1245-1255.
Cao, J., et al., "Incorporation and Clearance of Omega-3 Fatty Acids in Erythrocyte Membranes and Plasma Phospholipids." Clinical Chemistry 52(12):2265-2272 (2006).
Cao, Y., et al., Genomics, vol. 49, "Cloning, Expression, and Chromosomal Localization of Human Long-Chain Fatty Acid CoA Ligase 4 (FACL4)," pp. 327-330, 1998.
Capuzzi, et al. "Efficacy and Safety of an Extended-Release Niacin (Niaspan): A Long-Term Study," Am J Cardiol 1998;82:74U-81U.
Carlson, L.A. & Rosenhamer G. (1988). Reduction of mortaility in the Stockholm Ischaemic Heart Disease Secondary Prevention Study by combined treatment with clofibrate and nicotinic acid. Acta Med. Scand. 223, 405-418.
Carlson, L.A., Nicotinic acid: the broad-spectrum lipid drug. A 50$^{th}$ anniversary review, Journal of Internal Medicine, 2005: 258: 94-114.
Carrero et al., "Intake of Fish Oil, Oleic Acid, Folic Acid, and Vitamins B-6 and E for 1 Year Decreases Plasma C-Reactive Protein and Reduces Coronary Heart Disease Risk Factors in Male Patients in a Cardiac Rehabilitation Program", pp. 384-390, 2007.
Carroll, D. N., et al., "Evidence for the Cardioprotective Effects of Omega-3 Fatty Acids." Ann Pharmacother., 36:1950-6 (2002).

Cazzola, R., et al., "Age- and dose-dependent effects of an eicosapentaenoic acid-rich oil on cardiovascular risk factors in healthy male subjects." Atherosclerosis 193:159-167 (2007).
Cefali, E.A, et al., "Aspirin reduces cutaneous flushing after administration of an optimized extended-release niacin formulation." International Journal of Clinical Pharmacology and Therapeutics, vol. 45—No. 2/2007 (78-88).
Center for Drug Evaluation and Research. Omacor (Lovaza) Medical Reviews 2004 (last accessed May 29, 2008 at http://www.fda.gov/cder/foi/nda/2004/21-654_Omacor_Medr.pdf).
Center for Drug Evaluation and Research. Application No. 21-853, 21654s016, (Omacor). Statistical Review and Evaluation: Clinical Studies, Omacor (omega-3 acid ethyl ester) Capsules, 4 grams/day; 2007. Available at: http://www.accessdata.fda.gov/drugsatfda_docs/nda/2007/021853s000;%20021654s016_StatR.pdf. Accessed Jan. 26, 2012.
Center for Drug Evaluation and Research. Approval Package for: 21-654 (Omacor/Lovaza). Statistical Review; 2004. Available at: http://www.accessdata.fda.gov/drugsatfda_docs/nda/2004/21-654_Omacor_AdminCorres_P1.pdf. Accessed Jan. 26, 2012.
Chan et al., "Effect of Atorvastatin and Fish Oil on Plasma High-Sensitivity C-Reactive Protein Concentrations in Individuals with Visceral Obesity", Clin. Chem., vol. 48, pp. 877-883 (2002).
Chan, D.C., et al., "Randomized controlled trial of the effect of n-3 fatty acid supplementation on the metabolism of apolipoprotein B-100 and chylomicron remnants in men with visceral obesity." Am J Clin Nutr 77:300-7 (2003).
Chapman, M.J., et al., "Cholesteryl ester transfer protein: at the heart of the action of lipid-modulating therapy with statins, fibrates, niacin, and cholesteryl ester transfer protein inhibitors." Eur Heart J. 2010;31:149-164.
Chemical Book, Eicosapentaenoic acid ethyl ester, copyright 2010, printed Jun. 16, 2011 from www.chemicalbook.com.
Chen, H., et al., "Eicosapentanoic acid inhibits hypoxia-reoxygenation-induced injury by attenuating upregulation of MMP-1 in adult rat myocytes." Cardiovascular Research 59:7-13 (2003).
Chen, H., et al., "EPA and DHA attenuate ox-LDL-induced expression of adhesion molecules in human coronary artery endothelial cells via protein kinase B pathway." Journal of Molecular and Cellular Cardiology 35:769-775 (2003).
Chen, I.S., et al., "In vitro clearance of chylomicron triglycerides containing (ω-3) eicosapentaenoate." Atherosclerosis, 65:193-198 (1987).
Childs, M.T., et al., "Divergent lipoprotein Responses to Fish Oils With Various Ratios of Eicosapentaenoic Acid and Docasahexaenoic Acid", American Society for Clinical Nutrition, 52:632-9, 1990.
Christensen, J. H., et al., "Effect of fish oil on heart rate variability in survivors of myocardial infarction: a double blind randomised controlled trial." BMJ, 312:677-678 (1996).
Christensen, M.S., et al., "Intestinal absorption and lymphatic transport of eicosapentaenoic (EPA), docosahexaenoic (DHA), and decanoic acids: dependence on intramolecular triacyiglycerol structure." Am J Clin Nutr 61:56-61 (1995).
Cleland, L.G., et al., "A Biomarker of n-3 compliance in patients taking fish oil for rheumatoid arthritis." Lipids 38:419-424 (2003).
Clinical Trial NCT01047501, Effect of AMR101 (Ethyl Icosapentate) on Triglyceride (Tg) Levels in Patients on Statins With High Tg Levels (>200 and <500 mg/dL) (ANCHOR), ClinicalTrials.gov [database online], U.S. National Institute of Health, Jan. 2010 [retrieved Apr. 27, 2011], Retrieved from the Internet: <http://clinicaltrials.gov/ct2/show/NCT01047501>.
Cohen, J.D., et al., "30-year trends in serum lipids among United States adults: results from the National Health and Nutrition Examination Surveys II, III, and 1999-2006." Am J Cardiol. 2010;106:969-975.
Cole et al., "Challenges and opportunities in the encapsulation of liquid and semi-solid formulations into capsules for oral administration," Advanced Drug Delivery Reviews, vol. 60, No. 6, Dec. 21, 2007, pp. 747-756.
Colhoun, H. M., et al., "Primary prevention of cardiovascular disease with atorvastatin in type 2 diabetes in the Collaborative Atorvastatin Diabetes Study (CARDS): multicentre randomised placebo-controlled trial." Lancet 364: 685-9 (2004).

(56) References Cited

OTHER PUBLICATIONS

Collins, N., et al., "Differences between Dietary Supplement and Prescription Drug Omega-3 Fatty Acid Formulations: A Legislative and Regulatory Perspective." Journal of the American College of Nutrition, 27 (6):659-666 (2008).

Conklin, S. M., et al., "Serum ω-3 fatty acids are associated with variation in mood, personality and behavior in hypercholesterolemic community volunteers." Psychiatry Research 152: 1-10 (2007).

Connor et al., "Seminars in thrombosis and hemostasis" (1988) 14:271-284.

Connor, W.E., "Importance of n-3 Fatty Acids in Health and Disease", Am. J. Clin. Nutr., 71(1(S)):171S-175S, 2000.

Conquer, J.A., et al., "Effect of supplementation with different doses of DHA on the levels of circulating DHA as non-esterified fatty acid in subjects of Asian Indian background. J Lipid Res." 1998;39:286-292.

Conquer, J.A., et al., "Supplementation with an algae source of docosahexaenoic acid increases (n-3) fatty acid status and alters selected risk factors for heart disease in vegetarian subjects." J Nutr. 1996;126: 3032-3039.

Contacos et al. Effect of pravastatin and omega-3 fatty acids on plasma lipids and lipoproteins in patients with combined hyperlipidemia, pp. 1755-1762, 1993.

Criqui, M., "Triglycerides and Coronary Heart Disease Revisited (Again)," Sep. 18, 2007, vol. 147 No. 6, pp. 425-427.

Crowe, F. L., et al., "Serum phospholipid n-3 long-chain polyunsaturated fatty acids and physical and mental health in a population-based survey of New Zealand adolescents and adults." Am J Clin Nutr 86:1278-85 (2007).

Daggy, B., et al., Dietary fish oil decreases VLDL production rates. Biochimica et Biophysics Acta 920: 293-300 (1987).

Das, U.N., Essential fatty acids as possible mediators of the actions of statins. Prostaglandins, Leukotrienes and Essential FattyAcids 65(1):37-40, (2001).

Davidson MH, Stein EA, Bays HE et al. "Efficacy and tolerability of adding prescription omega-3 fatty acids 4 g/d to simvastatin 40 mg/d in hypertriglyceridemic patients: an 8-week, randomized, double-blind, placebo-controlled study," Clin Ther 2007; 29:1354-1367.

Davidson MH. (2006). "Mechanisms for the hypotriglyceridemic effect of marine omega-3 fatty acids." Am J Cardiol 98(4A):27i-33i.

Davidson, M.H., et al., "Effects of docosahexaenoic acid on serum lipoproteins in patients with combined hyperlipidemia: a randomized, doubleblind, placebo-controlled trial." J Am Coll Nutr. 1997;16:236-243.

De Caterina, R, et al., "Control of Endothelial Leukocyte Adhesion Molecules by Fatty Acids." Lipids, vol. 31:S57-S63 (1996).

De Caterina, R., et al., "The Omega-3 fatty acid docosahexaenoate reduces cytokine-induced expression of proatherogenic and proinflammatory proteins in human endothelial cells." Arterioscler. Thromb. Vasc. Biol. 14:1829-1836 (1994).

Deckelbaum,, R. J., et al., "Conclusions and recommendations from the symposium, Beyond Cholesterol: Prevention and Treatment of Coronary Heart Disease with n-3 Fatty Acids." Am J Clin Nutr 87:2010S-12S (2008).

Dewailly, E., et al., "n-3 Fatty acids and cardiovascular disease risk factors among the Inuit of Nunavik." Am J Clin Nutr 74:464-73 (2001).

Diagnostic and Statistical Manual of Mental Disorders, 4th. Ed, published by the American Psychiatric Assoc., pp. 285-286, 1994.

Diagnostic and Statistical Manual of Mental Disorders, 4th. Ed. text revision, published by the American Psychiatric Assoc., pp. 154-163, and 369-381, 2000.

Dijan, P., et al., Proc. Natl. Acad. Sci., vol. 93, "Codon repeats in genes associated with human diseases: Fewer repeats in the genes of nonhuman primates and nucleotide substitutions concentrated at the sites of reiteration," pp. 417-421, Jan. 1996.

Dijk, J. M., et al., "Carotid intima-media thickness and the risk of new vascular events in patients with manifest atherosclerotic disease: the SMART study." European Heart Journal 27:1971-1978 (2006).

Dodin, S., et al., "Flaxseed on cardiovascular disease markers in healthy menopausal women: a randomized, double-blind, placebo-controlled trial." Nutrition 24:23-30 (2008).

Dolecek, D.A., "Epidemiological Evidence of Relationships Between Dietary Polysunsaturated Fatty Acids and Morality in the Multiple Risk Factor Intervention Trial", Society of Experimental Biology and Medicine, 200(2):177-182, 1991.

Dullenmeijer, C., et al., "n-3 Fatty acid proportions in plasma and cognitive performance in older adults." Am J Clin Nutr 86:1479-85 (2007).

Duncan, R. E., et al., "Regulation of HMG-CoA reductase in MCF-7 cells by genistein, EPA, and DHA, alone and in combination with mevastatin." Cancer Letters 224:221-228 (2005).

Durrington PN et al. "An omega-3 poly unsaturated fatty acid concentrate administered for one year decreased triglycerides in simvastatin treated patients with coronary heart disease and persistent Hypertriglyceridemia," Heart 2001; 85:544-48.

Dwyer, J. H., et al., "Arachidonate 5-Lipoxygenase Promoter Genotype, Dietary Arachidonic Acid, and Atherosclerosis." N. Engl. J. Med., 350:1 (2004).

Dyerberg, J., et al., "Marine Oils and Thrombogenesis." Prog. Lipid Res. 21:255-269 (1982).

Egert, S., et al., "Dietary alpha-linolenic acid, EPA, and DHA have differential effects on LDL fatty acid composition but similar effects on serum lipid profiles in normolipidemic humans." J Nutr. 2009;139:861-868.

Eisenberg S, Bilheimer DW, Levy RI, Lindgren FT. "On the metabolic conversion of human plasma very low density lipoprotein to low density lipoprotein," Biochim Biophys Acta 1973; 326:361-77.

Eisenberg S, Rachmilewitz D. "Metabolism of rat plasma very low density lipoprotein. I. Fate in circulation of the whole lipoprotein," Biochim Biophys Acta 1973; 326:378-90.

Elam et al., Effect of Niacin on Lipid and Pipoprotein Levels and Glycemic Control in Patients With Diabetes and Peripheral Arterial Disease: The ASMIT Study: A Randomized Trial, JAMA, 2000;284(10); 1263-1270.

El-Sohemy, A., et. al., "Regulation of Mevalonate Synthesis in Low Density Lipoprotein Receptor Knockout Mice Fed n-3 or n-6 Polyunsaturated Fatty Acids." Lipids, 34 (10): 1037-43 (1999).

Engler, et al., "Docosahexaenoic acid restores endothelial function in children with hyperlipidemia: results from the EARLY Study." International Journal of Clinical Pharmacology and Therapeutics, vol. 42—No. Dec. 2004 (672-679).

Engler, M.B., et al., "Mechanisms of vasorelaxation induced by eicosapentaenoic acid (20:5n-3) in WKY rat aorta." British Journal of Pharmacology 131:1793-1799 (2000).

Engler, M.M., et al., "The effects of a diet rich in docosahexaenoic acid on organ and vascular fatty acid composition in spontaneously hypertensive rats." Prostaglandins, Leukotrienes and Essential Fatty Acids 61(5):289-295 (1999).

Epadel® [Complete prescribing information]. Update (Version 5). Tokyo, Japan: Mochida Pharmaceutical; Jan. 2007. (English translation).

Faggin, E., et al., "Fish Oil Supplementation Prevents Neointima Formation in Nonhypercholesterolemic Balloon-Injured Rabbit Carotid Artery by Reducing Medial and Adventitial Cell Activation." Arterioscler. Thromb. Vasc. Biol., 20:152-163 (2000).

Fer, M., et al., "Metabolism of eicosapentaenoic and docosahexaenoic acids by recombinant human cytochromes P450." Archives of Biochemistry and Biophysics 471:116-125 (2008).

Ferns, G., et al., "Investigation and management of hypertriglyceridaemia." J. Clin. Pathol. 61:1174-1183 (2008).

Finnen, M.J., et al., Biochemical Society Trans., "Purification and characterization . . . ", p. 19, 1991.

Fisher et al., Journal of Biological Chemistry (2001) 276(3) 27855-27863.

Fischer, R., et al., "Dietary n-3 polyunsaturated fatty acids and direct renin inhibition improve electrical remodeling in a model of high human renin hypertension." Hypertension 51:540-546 (2008).

Flaten, H., et al., "Fish-oil concentrate: effects on variables related to cardiovascular disease." Am. J. Clin. Nutr. 52:300-306 (1990).

Ford, E.S. et al., "Hypertriglyceridemia and Its Pharmacologic Treatment Among US Adults." Arch, Intern. Med., 169(6): 572-78 (2009).

(56) References Cited

OTHER PUBLICATIONS

Frick, M.H., et al., (1987) Helsinki Heart Study Primary prevention trial with gemfibrozil in middle-aged men and dyslipidaemia, afety of treatment, changes in risk factors and incidence of coronary heat disease. N. Eng. J. Med. 317: 1237-1245.

Friedewald, W.T., et al., "Estimation of the concentration of low-density lipoprotein cholesterol in plasma, without use of the preparative ultracentrifuge." Clin Chem. 1972;18:499-502.

Friedman, A. N., et al., "Fish Consumption and Omega-3 Fatty Acid Status and Determinants in Long-Term Hemodialysis." Amer. J. Kidney Diseases, 47(6):1064-1071 (2006).

Frøyland, L., et al., "Hypotriacylglycerolemic component of fish oil." Prostaglandins, Leukotrienes and Essential Fatty Acids 57 (4 & 5):387-388 (1997).

Garg et al., "Niacin treatment increases plasma homocyst(e)ine levels," Am Heart J 1999;138:1082-7.

Garnett, WR, Am J Health-Sys Pharm vol. 52 (1995); 1639-1645.

Genest, J.J., et al., (1992) Familial lipoprotein disorders in patients with premature coronary artery disease, Circulation. 85: 2025-2033.

Geppert, et al. "Microalgal docosahexaenoic acid decreases plasma triacylglycerol in normolipidaemic vegetarians: a randomized trial." British Journal of Nutrition (2006), 95, 779-786.

Gillies, et al. "Effect of a Novel Eicosapentaenoic Acid-Rich Oil on Serum Cholesterol in Man," DuPont 2010.

Ginsberg HN. "Hypertriglyceridemia: new insights and new approaches to pharmacologic therapy," Am J Cardiol 2001; 87:1174-1180.

GISSI-Prevenzione Investigators, "Dietary Supplementation with n-3 Polyunsaturated Fatty Acids and Vitamin E after Myocardial Infarction: Results of the GISSI-Prevenzione Trial", The Lancet, 354:447-455, Aug. 7, 1999.

Glod, "Recent Advances in the Pharmacacotherapy of Major Depression", Arch. Psychiatr. Nurs. Dec. 1996 10(6):355-364. (Abstract Only).

Goldberg, A C: "Combination therapy of dyslipidemia," Current Treatment Options in Cardiovascular Medicine 200708 GB, vol, 9, No. 4, Aug. 2007, pp. 249-258.

Gordon, D.J., et al., (1989) High density lipoprotein cholesterol and cardiovascular disease: four prospective American studies. Circulation, 79: 8-15.

Gorriz JL et al. (1996) "Rhabdomyolysis and Acute Renal Failure Associated with Gemfibrozil Therapy," Nephron 74(2): 437-438.

Gorriz, JL (1995) "Rhabdomyolysis and Acute Renal Failure Associated with Bezafibrate Treatment," Nephrol Dial Transplant 10(12):2371-2372.

Goto, Y., et al., "Clinical Pharmacological Trial of Ethyl Icosapentate (MND-21)—Dose Finding Study." Journal of Clinical Therapeutic & Medicines 8:1293-309 (1992).

Gould, A.L., et al., "Cholesterol reduction yields clinical benefit: impact of statin trials." Circulation. 1998;97:946-952.

Grenyer, Brin F.S., et al., "Fish Oil Supplementation in the Treatment of Major Depression: A Randomised Double-Blind Placebo-Controlled Trial" Progress in Neuro-Psychopharmacology & Biological Psychiatry 31:1393-1396 (2007).

Griffin, M.D., et al., "Effects of altering the ratio of dietary n-6 to n-3 fatty acids on insulin sensitivity, lipoprotein size, and postprandial lipemia in men and postmenopausal women aged 45-70 y: the OPTILIP Study." Am J Clin Nutr 84:1290-8 (2006).

Grimsgaard, S., et al., "Effects of Highly Purified Eicosapentaenoic Acid and Docosahexaenoic Acid on Hemodynamics in Humans" American Society for Clinical Nutrition, 68:52-9, 1998.

Grimsgaard, S., et al., "Highly purified eicosapentaenoic acid and docosahexaenoic acid in humans have similar triacylglycerol-lowering effects but divergent effects on serum fatty acids" Am. J. Clin. Nutr., 66:649-59, 1997.

Grundy et al., Efficacy, Safety, and Tolerability of Once-Daily Niacin for the Treatment of Dyslipidemia Associated with Type 2 Diabetes, Arch Intern Med. 2002;162:1568-1572.

Guallar, E., et al., "Omega-3 fatty acids in adipose tissue and risk of myocardial infarction—The EURAMIC study." Arterioscler. Thromb. Vasc. Biol., 19:1111-1118 (1999).

Guillot, et al., "Increasing intakes of the long-chain ω-3 docosahexaenoic acid: effects on platelet functions and redox status in healthy men," The FASEV Journal, vol. 23, Sep. 2009, pp. 2909-2916.

Guizy, M., et al., "ω-3 and ω-6 Polyunsaturated fatty acids block *HERG* channels." Am J Physiol Cell Physiol 289:C1251-C1260 (2005).

Gyarmathy, M., "Selection from the industrial manufacturing. $5^{th}$ part: Gelatine capsules. 5/2 part: Soft gelatine capsules," Gyogyszereszet, vol. 38, No. 2, Feb. 1, 1994, pp. 105-109.

Hall, W. L., et al., "A high-fat meal enriched with eicosapentaenoic acid reduces postprandial arterial stiffness measured by digital volume pulse analysis in healthy men." J. Nutr. 138: 287-291 (2008).

Hamazaki et al., "Effects of Orally Administered Ethyl Ester of Eicosapentaenoic Acid (EPA: C20:5, omega-3) on PGI2-Like Substance Production by Rat Aorta" Prostaglandins, Apr. 1982, vol. 23 No. 4, pp. 557-567.

Hamazaki T. et al., "Reduction of microalbuminuria in diabetics by Eicosapentaenoic acid ethyl ester" Lipids. 25 (9):542-5 (Sep. 1990).

Hamazaki, T., et al., "Docosahexaenoic Acid-Rich Fish Oil Does Not Affect Serum Lipid Concentrations of Normolipidemic Young Adults", American Institute of Nutrition, 126(11):2784-2789, Nov. 1996.

Han, J. J., et al., "Enhancement of both reaction yield and rate of synthesis of structured triacylglycerol containing eicosapentaenoic acid under vacuum with water activity control." Lipids 34:989-995 (1999).

Hanasaki, K., et al., "Potent modification of low density lipoprotein by group X secretory phospholipase A2 is linked to macrophage foam cell formation." J. Biol. Chem. 277(32):29116-24 (2002).

Haney, E.M., et al., "Screening for lipid disorders in children and adolescents; Systematic evidence review for the U.S. Preventive Services Task Force (evidence synthesis)." No. 47. Rockville, MD: Agency for Healthcare Research and Quality, US Department of Health and Human Services; AHRQ Publication No. 07-0598-EF-1; Jul. 2007. Available at: http://www.uspreventiveservicestaskforce.org/uspstf07/chlipid/chlipidsyn.pdf. Accessed Mar. 23, 2011.

Hannah, J., et al., "Effect of dietary fatty acids on LDL binding." Ann N Y Acad Sci. 1993; 683:178-182.

Hansen, J.B., et al., "Effects of highly purified eicosapentaenoic acid and docosahexaenoic acid on fatty acid absorption, incorporation into serum phospholipids and postprandial triglyeridemia." Lipids 33:131-38 (1998).

Harkonarson, H., et al., "Effects of a 5-lipoxygenase-activating protein inhibitor on biomarkers associated with risk of myocardial infarction—a randomized trial." JAMA, 293(8):2245-56 (2005).

Harris, W. S. et al. "Safety and efficacy of Omacor in severe hypertriglyceridemia," Journal of Cardiovascular Risk 1997, 4:385-391.

Harris, W. S., "Fish oils and plasma lipid and lipoprotein metabolism in humans: a critical review." J Lipid Res. 30:785-807 (1989).

Harris, W. S., "The omega-3 index as a risk factor for coronary heart disease." Am J Clin Nutr 87:1997S-2002S (2008).

Harris, W. S., et al., "Influence of n-3 fatty acid supplementation on the endogenous activities of plasma lipasas." Am. J. Clin. Nutr. 66:254-60 (1997).

Harris, W. S., et al., "n-3 Fatty acids and urinary excretion of nitric oxide metabolites in humans." Am. J. Clin. Nutr., 65:459-64 (1997).

Harris, W.S., "Expert opinion: omega-3 fatty acids and bleeding—cause for concern?" The American Journal of Cardiology 99(6A): 45C-46C (2007).

Harris, W.S., "n-3 Fatty acids and human lipoprotein metabolism: an update." Lipids 34:S257-S258 (1999).

Harris, W.S., "n-3 Fatty acids and serum lipoproteins: human studies." Am J Clin Nutr 65:1645S-54S (1997).

Harris, W.S., "Omega-3 fatty acids in cardiac biopsies from heart transplantation patients." Circulation 110;1645-1649 (2004).

Harris, W.S., et al., "Comparison of the effects of fish and fish-oil capsules on the n-3 fatty acid content of blood cells and plasma phospholipids." Am J Clin Nutr 86:1621-5 (2007).

(56) References Cited

OTHER PUBLICATIONS

Harris, W.S., et al., "Omega-3 fatty acids and coronary heart disease risk: Clinical and mechanistic perspectives." Atherosclerosis 197:12-24 (2008).
Harris, W.S., et al., "Stearidonic acid increases the red blood cell and heart eicosapentaenoic acid content in dogs." Lipids 42:325-333 (2007).
Harris, W.S., et al., "Tissue n-3 and n-6 fatty acids and risk for coronary heart disease events." Atherosclerosis 193:1-10 (2007).
Hartweg, J., et al., "Potential impact of omega-3 treatment on cardiovascular disease in type 2 diabetes." Curr Opin Lipidol. 2009; 20:30-38.
Hawthorne, et al., "High dose eicosapentaenoic acid ethyl ester: effects on lipids and neutrophil leukotriene production in normal volunteers." Br. J. Clin. Pharmac. (1990), 30, 187-194.
Hayashi et al., Decreases in Plasma Lipid Content and Thrombotic Activity by Ethyl Icosapentate Purified from Fish Oiles, Current Therapeutic Research, vol. 56, No. 1, Jan. 1995, pp. 24-31.
Hibbeln, J. R., et al., "Healthy intakes of n-3 and n-6 fatty acids: estimations considering worldwide diversity." Am J Clin Nutr. 83:1483S-93S (2006).
Hilpert, K.F., et al., "Postprandial effect of n-3 polyunsaturated fatty acids on apolipoprotein B-containing lipoproteins and vascular reactivity in type 2 diabetes." Am J Clin Nutr 85:369-76 (2007).
Hirafuji, M., et al., "Docosahexaenoic acid potentiates interleukin-1beta induction of nitric oxide synthase through mechanism involving p44/42 MAPK activation in rat vascular smooth muscle cells." British Journal of Pharmacology 136:613-619 (2002).
Hirai, A., et al., (1982). The effects of the oral administration of fish oil concentrate on the release and the metabolism of [$^{14}$C] arachidonic acid and [$^{14}$C] eicosapentaenoic acid by human platelets. Thromb. Res. 28: 285-298.
Hirano, R., et al., "Regulation by long-chain fatty acids of the expression of cholesteryl ester transfer protein in HepG2 cells." Lipids. 2001; 36:401-406.
Holmeide, A. K., et al., "Oxidative degradation of eicosapentaenoic acid into polyunsaturated aldehydes." Tetrahedron 59:7157-7162 (2003).
Holub, B.J., PhD, "Fish Oils and Cardiovascular Disease", Canadian Medical Association Journal, 141(10):1063, Nov. 15, 1989.
Hombeck, M., et al., "Biosynthesis of the algal pheromone fucoserratene by the freshwater diatom *Asterionella formosa* (Bacillariophyceae)." Tetrahedron 54:11033-11042 (1998).
Hoskins et al., Combination use of statins and omega-3 fatty acids: an emerging therapy for combined hyperlipidemia, pp. 579-591—Abstract only, 2006.
Howe, P.R.C., et al., "Equal antithrombotic and triglyceride-lowering effectiveness of eicosapentaenoic acid-rich and docosahexaenoic acid-rich fish oil supplements." Lipids 34:S307-S308 (1999).
Huntingdon's Disease Drug Works, The DHA Dilemma, available at http://hddrugworks.org/index.php?option=com_content&task=view&id=185&Itemid=26, printed on Aug. 22, 2008.
Illingworth et al., "Comparative Effects of Lovastatin and Niacin in Primary Hypercholesterolemia. A Prospective Trial," Arch Intern med. 1994;154:1586-1595.
Inoue, I., et al., "Expression of peroxisome proliferator-activated receptor α (PPARα) in primary cultures of human vascular endothelial cells." Biochem. Biophys. Res. Comm., 246, 370-374 (1998).
Ishida, Y., et al., "α-Lipoic Acid and Insulin Autoimmune Syndrome." Diabetes Care, 30(9): 2240-41 (2007).
Isley, et al., "Pilot study of combined therapy with ω-3 fatty acids and niacin in atherogenic dyslipidemia," Journal of Clinical Lipidology (2007) 1, 211-217.
Jacobson et al. "Hypertriglyceridemia and Cardiovascular Risk Reduction", Clinical Therapeutics, vol. 29 pp. 763-777 (2007).
Jacobson, T. Secondary Prevention of Coronary Artery Disease with Omega-3 Fatty Acids. Am J Cardiol 2006; 98 [suppl]: 61i-70i.
Jacobson, T.A., "Role of n-3 fatty acids in the treatment of hypertriglyceridemia and cardiovascular disease." Am J Clin Nutr 87:1981S-90S (2008).
Jacobson, T.A., et al., "Effects of eicosapentaenoic acid and docosahexaenoic acid on low-density lipoprotein cholesterol and other lipids: A review." J. Clin. Lipidology, vol. 6, pp. 5-18 (2012).
Jenner, "Presymptomatic Detection of Parkinson's Disease". J Neural Transm Suppl, 1993; 40:23-36. (Abstract only).
Jialal, I., "Editorial: Remnant lipoproteins: measurement and clinical significance." Clinical Chemistry 48(2):217-219 (2002).
Jung, U.J., et al., "n-3 Fatty acids and cardiovascular disease: mechanisms underlying beneficial effects." Am J Clin Nutr 87: 2003S-9S (2008).
Kanayasu, T., et al., "Eicosapentaenoic acid inhibits tube formation of vascular endothelial cells in vitro." Lipids 26:271-276 (1991).
Katan, M. B., et al., "Kinetics of the incorporation of dietary fatty acids into serum cholesteryl esters, erythrocyte membranes, and adipose tissue: an 18-month controlled study." J. Lipid Res. 38: 2012-2022 (1997).
Katayama et al. Prog. Med.(2001) 21:457-467, translated from Japanese.
Kato, T., et al., "Palmitate impairs and eicosapentaenoate restores insulin secretion through regulation of SREBP-1c in pancreatic islets." Diabetes, 57(9):2382-2392 (2008) (published online May 5, 2008.).
Kawano, H., et al., (2002). Changes in aspects such as the collagenous fiber density and foam cell size of atherosclerotic lesions composed of foam cells, smooth muscle cells and fibrous components in rabbits caused by all-cis-5,8,11,14,17-icosapentaenoic acid. J. Atheroscler. Thromb. 9: 170-177.
Kawashima, H., et al., "Oral Administration of Dihomo-γ-Linolenic Acid Prevents Development of Atopic Dermatitis in NC/Nga Mice." Lipids 43:37-43 (2008).
Kelley, D. S., et al., "Docosahexaenoic Acid Supplementation Decreases Remnant-Like Particle-Cholesterol and Increases the (n-3) Index in Hypertriglyceridemic Men." J. Nutr. 138: 30-35 (2008).
Kelley, et al., "Docosahexaenoic acid supplementation improves fasting and postprandial lip profiles in hypertriglyceridemic men." The American Journal of Clinical Nutrition, 2007; 86: 324-333.
Kew, S., et al., "Effects of oils rich in eicosapentaenoic and docosahexaenoic acids on immune cell composition and function in healthy humans." Am J Clin Nutr 79:674-81 (2004).
Kimura, F., et al., "Long-term supplementation of docosahexaenoic acid-rich, eicosapentaenoic acid-free microalgal oil in n-3 fatty acid-deficient rat pups." Biosci. Biotechnol. Biochem., 72(2):608-610 (2008).
Kinsella, J.E., et al., "Dietary n-3 polyunsaturated fatty acids and amelioration of cardiovascular disease: possible mechanisms." Am J Clin Nutr 52:1-28 (1990).
Knopp et al., "Contrasting Effects of Unmodified and Time-Release Forms of Niacin on Lipoproteins in Hyperlipidemic Subjects: Clues to Mechanism of Action of Niacin," Northwest Lipid Research Clinic, Department of Medicine, School of Medicine, University of Washington, Seattle, 1985, pp. 642-650.
Kohno, M., et al., "Inhibition by Eicosapentaenoic Acid of Oxidized-LDL- and Lysophosphatidylcholine-Induced Human Coronary Artery Smooth Muscle Cell Production of Endothelin." J. Vasc. Res. 38:379-388 (2001).
Kojima, T,. et al., "Long-term administration of highly purified eicosapentaenoic acid provides improvement of psoriasis." Dermatologica, 182:225-230 (1991).
Kosonen, O., et al., "Inhibition by nitric oxide-releasing compounds of E-selectin expression in and neutrophil adhesion to human endothelial cells." European Journal of Pharmacology 394:149-156 (2000).
Kris-Ehterton, P. M., et al., "Omega-3 Fatty Acids and Cardiovascular Disease—New Recommendations From the American Heart Association." Arterioscler Thromb Vasc Biol. 23:151-152 (2003).
Kris-Etherton, P.M., et al., "American Heart Association Nutrition Committee. Fish consumption, fish oil, omega-3 fatty acids, and cardiovascular disease." Circulation. 2002;106:2747-2757.

(56) References Cited

OTHER PUBLICATIONS

Ku, K., et al., "Beneficial Effects of to-3 Fatty Acid Treatment on the Recovery of Cardiac Function After Cold Storage of Hyperlipidemic Rats." Metabolism, 48(10):123-1209 (1999).

Kurabayashi, T., et al., "Eicosapentaenoic acid effect on hyperlipidemia in menopausal Japanese women." Obstet Gynecol 96:521-8 (2000).

Lai et al., Suppression of Niacin-induced Vasodilation with an Antagonist to Prostaglandin $D_2$ Receptor Subtype 1, clinical Pharmacology & Therapeutics, vol. 81, No. 6, Jun. 2007, pp. 849-857.

Laidlaw, M., et al., "Effects of supplementation with fish oil-derived n-3 fatty acids and γ-linolenic acid on circulating plasma lipids and fatty acid profiles in women." Am J Clin Nutr 77:37-42 (2003).

Larsen, L.N., et al., "Heneicosapentaenoate (21:5n-3): Its incorporation into lipids and its effects on arachidonic acid and eicosanoid Synthesis." Lipids 32:707-714 (1997).

Law, M.R., et al., "Quantifying effect of statins on low density lipoprotein cholesterol, ischaemic heart disease, and stroke: systematic review and meta-analysis." Br Med J. 2003;326:1423-1427.

Leaf, A., "Historical overview of n3 fatty acids and coronary heart disease." Am J Clin Nutr 87:1978S-80S. (2008).

Lee, J.H., et al., "Omega-3 fatty acids for cardioprotection." Mayo Clin Proc., 83(3):324-332 (2008).

Lee, K.W., et al., "The Role of Omega-3 Fatty Acids in the Secondary Prevention of Cardiovascular Disease", Q J Med, 96:465-480, 2003.

Lemaitre, R.N., et al., "n-3 Polyunsaturated fatty acids, fatal ischemic heart disease, and nonfatal myocardial infarction in older adults: the Cardiovascular Health Study." Am J Clin Nutr 77:319-25 (2003).

Leonard, B.E., Fundamentals of Psychopharmacology, pp. 186-187, 1997.

Leucht, S., et al., Schizophrenia Research, vol. 35, "Efficacy and extrapyramidal side-effects of the new antipsychotics olanzapine, quetiapine, risperidone, and sertindole compared to conventional antipsychotics and placebo. A meta-analysis of randomized controlled trials", pp. 51-68, 1999.

Li, D., et al., "Effect of dietary a-linolenic acid on thrombotic risk factors in vegetarian men." Am J Clin Nutr 69:872-82 (1999).

Li, H., et al., "EPA and DHA reduce LPS-induced inflammation responses in HK-2 cells: Evidence for a PPAR-γ-dependent mechanism." Kidney Int'l 67:867-74 (2005).

Lien, E.L., "Toxicology and safety of DHA." Prostaglandins Leukot Essent Fatty Acids. 2009;81:125-132.

Lin, Pao-Yen, M.D., et al. "A Meta-Analytic Review of Double-Blind, Placebo-Controlled Trials of Antidepressant Efficacy of Omega-3 Fatty Acids", Psychiatry, 1056-1061 (Jul. 2007).

Lin, Y., et al., "Differential effects of eicosapentaenoic acid on glycerolipid and apolipoprotein B metabolism in primary human hepatocytes compared to HepG2 cells and primary rat hepatocytes." Biochimica et Biophysica Acta 1256:88-96 (1995).

Lindsey, S., et al., "Low density lipoprotein from humans supplemented with n-3 fatty acids depresses both LDL receptor activity and LDLr mRNA abundance in HepG2 cells." J Lipid Res. 1992;33:647-658.

Lipitor (Pfizer, 2007).

Lohmussaar, E., et al., "ALOX5AP Gene and the PDE4D Gene in a Central European Population of Stroke Patients." Stroke, 36:731-736 (2005).

LOVAZA® (omega-3-acid ethyl esters) Capsules, Prescribing information, 12 pgs., Jun. 2008, GlaxoSmithKline.

LOVAZA (Smith Kline Beechum, Jul. 2009).

Lu, G., et al., "Omega-3 fatty acids alter lipoprotein subfraction distributions and the in vitro conversion of very low density lipoproteins to lowdensity lipoproteins." J Nutr Biochem. 1999;10:151-158.

Lucas, M., et al., "Ethyl-eicosapentaenoic acid for the treatment of psychological distress and depressive symptoms in middle-aged women: a double-blind, placebo-controlled, randomized clinical trial." Am J Clin Nutr 89:641-51 (2009).

Luria, M. "Effect of Low-Dose Niacin on High-Density Lipoprotein Cholesterol and Total Cholesterol/High-Density Lipoprotein Cholesterol Ratio," Arch Intern Med 1988;148:2493-2495.

Madhavi, N., et al., "Effect of n-6 and n-3 fatty acids on the survival of vincristine sensitive and resistant human cervical carcinoma cells in vitro", Cancer Letters, vol. 84, No. 1, 1994, pp. 31-41.

Madsen, L., et al., "Eicosapentaenoic and Docosahexaenoic Acid Affect Mitochondrial and Peroxisomal Fatty Acid Oxidation in Relation to Substrate Preference." Lipids 34:951-963 (1999).

Maki, K.C., et al., "Baseline lipoprotein lipids and low-density lipoprotein cholesterol response to prescription omega-3 acid ethyl ester added to simvastatin therapy." Am J Cardiol. 2010;105:1409-1412.

Maki, PhD, et al., "Lipid Responses to a Dietary Docosahexaenoic Acid Supplement in Men and Women with Below Average Levels of High Density Lipoprotein Cholesterol." Journal of the American College of Nutrition, vol. 24, No. 3, 189-199 (2005).

Mallat, Z., et al., "Apoptosis in the vasculature: mechanisms and functional importance." British Journal of Pharmacology 130:947-962 (2000).

Mallat, Z., et al., "Protective role of interleukin-10 in atherosclerosis." Circ. Res. 85:e17-e24 (1999).

Marangell, L. B., et al., "A Double-Blind, Placebo-Controlled Study of the Omega-3 Fatty Acid Docosahexaenoic Acid in the Treatment of Major Depression" Am J Psychiatry, 160(5):996-998, (May 2003).

Marckmann, P., "Fishing for heart protection." Am J Clin Nutr, 78:1-2 (2003).

Martin-Jadraque, R., et al., "Effectiveness of Low-Dose Crystalline Nicotinic Acid in Men With Low High-Density Lipoprotein Cholesterol Levels." Arch. Intern. Med., vol. 156, pp. 1081-1088 (May 27, 1996).

Mater, M.K., et al., "Arachidonic acid inhibits lipogenic gene expression in 3T3-L1 adipocytes through a prostanoid pathway." J. Lipid Res. 39:1327-1334 (1998).

Matsumoto, M., et al., "Orally administered eicosapentaenoic acid reduces and stabilizes atherosclerotic lesions in ApoE-deficient mice." Atherosclerosis, 197(2):524-533 (2008).

Matsuzawa, Y., et al., "Effect of Long-Term Administration of Ethyl Icosapentate (MND-21) in Hyperlipaemic Patients," J. Clin Therapeutic & Medicines 1991; 7: 1801-16.

Mayatepek, E., et al., The Lancet, vol. 352, "Leukotriene C4-synthesis deficiency: a new inborn error of metabolism linked to a fatal developmental syndrome" pp. 1514-1517, Nov. 7, 1998.

McElroy, S.L., et al., "Clozapine in the Treatment of Psychotic Mood Disorders, Schizoaffective Disorder, and Schizophrenia", Journal of Clinical Psychiatry, vol. 52, No. 10, Oct. 1991, pp. 411-414.

McKenney, James et al., "Role of prescription omega-3 fatty acids in the treatment of Hypertriglyceridemia," Pharmacotherapy, May 2007 LNKD—Pubmed: 17461707, vol. 27, No. 5, pp. 715-728.

McMurchie, E.J., et al., "Incorporation and effects of dietary eicosapentaenoate (20 : 5( n - 3)) on plasma and erythrocyte lipids of the marmoset following dietary supplementation with differing levels of linoleic acid." Biochimica et Biophysics Acta, 1045:164-173 (1990).

Menuet, R. et al., "Importance and management of dyslipidemia in the metabolic syndrome," American Journal of the Medical Sciences US, vol. 33, No. 6, Dec. 2005, pp. 295-302.

Merched, A.J., et al., "Atherosclerosis: evidence for impairment of resolution of vascular inflammation governed by specific lipid mediators." FASEB J. 22:3595-3606 (2008).

Mesa, M., "Effects of oils rich in Eicosapentaenoic and docosahexaenoic acids on the oxidizability and thrombogenicity of low-density lipoprotein," Artherosclerosis 175 (2004) 333-343.

Metcalf, R.G. et al., "Effect of dietary n-3 polyunsaturated fatty acids on the inducibility of ventricular tachycardia in patients with ischemic cardiomyopathy." Am J Cardiol 101:758-761 (2008).

Metcalf, R.G., et al., "Effects of fish-oil supplementation on myocardial fatty acids in humans." Am J Clin Nutr 85:1222-28 (2007).

Meyer, et al., "Dose-Dependent Effects of Docosahexaenoic Acid Supplementation on Blood Lipids in Statin-Treated Hyperlipidaemic Subjects." Lipids (2007) 42:109-115.

(56) References Cited

OTHER PUBLICATIONS

Meyers et al., Nicotinic acid induces secretion of prostaglandin $D_2$ in human macrophages: An in vitro model of the niacin flush, Artherosclerosis 192 (2007) 253-258.

Mii, S., et al., "Perioperative use of eicosapentaenoic acid and patency of infrainguinal vein bypass: a retrospective chart review." Curr Ther Res Clin Exp. 68:161-174 (2007).

Miles, et al., "Effect of orlistat in overweight and obese patients with type 2 diabetes treated with metformin," Diabetes Care, Jul. 2002 ; 25(7):1123-1128.

Miller, M., et al., "Impact of lowering triglycerides on raising HDL-C in hypertriglyceridemic and non-hypertriglyceridemic subjects." International Journal of Cardiology 119:192-195 (2007).

Minihane, A.M., et al., "ApoE polymorphism and fish oil supplementation in subjects with an atherogenic lipoprotein phenotype." Arterioscler. Thromb. Vasc. Biol. 20:1990-1997 (2000).

Mishra, A., et al., "Oxidized omega-3 fatty acids inhibit NF-κB activation via a PPARα-Dependent Pathway." Arterioscler Thromb Vasc Biol. 24:1621-1627 (2004).

Mita, T. et al., Eicosapentaenoic acid reduces the progression of carotid intima-media thickness in patients with type 2 diabetes, Atherosclerosis 191 (2007) 162-167.

Mizota M, Katsuki Y, Mizuguchi K, Endo S, Miyata H, Kojima M, Kanehiro H et al. "Pharmacological studies of eicosapentaenoic acid ethylester (EPA-E) on high cholesterol diet-fed rabbits," Nippon Yakurigaku Zasshi 1988; 91:255-66.

Mizota M, Katsuki Y, Mizuguchi K, Endo S, Miyata H, Kojima M, Kanehiro H et al. "The effects of eicosapentaenoic acid ethylester (EPA-E) on arterial thrombosis in rabbits and vascular lesions in rats," Nippon Yakurigaku Zasshi 1988; 91:81-9.

Mizuguchi K, Yano T, Kojima M, Tanaka Y, Ishibashi M, Masada A, Sato M et al. "Hypolipidemic effect of ethyl all-cis-5,8,11,14,17-eicosapentaenoate (EPA-E) in rats," Jpn J Pharmacol 1992; 59:3307-12.

Mizuguchi, K., et al., "Ethyl all-cis-5,8,11,14,17-icosapentaenoate modifies the biochemical properties of rat very low-density lipoprotein." European Journal of Pharmacology, 231:221-227 (1993).

Mizuguchi, K., et al., "Mechanism of the lipid-lowering effect of ethyl all-cis-5,8,11,14,17-icosapentaenoate." European Journal of Pharmacology, 231:121-127 (1993).

Mora, S., et al., "LDL particle subclasses, LDL particle size, and carotid atherosclerosis in the Multi-Ethnic Study of Atherosclerosis (MESA)." Atherosclerosis. 2007;192:211-217.

Mori TA, Woodman RJ. "The independent effects of eicosapentaenoic acid and docosahexaenoic acid on cardiovascular risk factors in humans," Curr Opin Clin Nutr Metab Care 2006; 9:95-104.

Mori, et al., "Purified Eicosapentaenoic and docosahexaenoic acids have differential effects on serum lipids and lipoproteins, LDL particle size, glucose, and insulin in mildly hyperlipidemic men," Am J Clin Nutr 2000; 71:1085-1094.

Mori, T. et al., Effect of Eicosapentaenoic acid and docosahexaenoic acid on oxidative stress and inflammatory markers in treated-hypertensive type 2 diabetic subjects, Free Radical Biology & Medicine, vol. 35, No. 7, pp. 772-781, 2003.

Mori, T., et al., "Docosahexaenoic Acid but Not Eicosapentaenoic Acid Lowers Ambulatory Blood Pressure and Heart Rate in Humans" Hypertension, (Aug. 1999).

Morita, I., et al., "Effects of purified eicosapentaenoic acid on arachidonic acid metabolism in cultured murine aortic smooth muscle cells, vessel walls and platelets." Lipids 18:42-490 (1983).

Morrow et al., Release of Markedly Increased Quantities of Prostaglandin D2 In Vivo in Humans Following the Administration of Nicotinic Acid, Prostaglandins, Aug. 1989, vol. 38, No. 2., pp. 263-274.

Morton, R.E., "Specificity of lipid transfer protein for molecular species of cholesteryl ester." J Lipid Res. 1986;27:523-529.

Mosher LR et al., "Nicotinic Acid Side Effects and Toxicity: A review," Am J Psychiat. 1970; 126: 1290-1296.

Mostad, I.L, et al., "Effects of n-3 fatty acids in subjects with type 2 diabetes: reduction of insulin sensitivity and time-dependent alteration from carbohydrate to fat oxidation." Am J Clin Nutr 84:540-50 (2006).

Mozaffarian, "JELIS, fish oil, and cardiac events," The Lancet, vol. 369, Mar. 31, 2007, pp. 1062-1063.

Mozaffarian, D., "Fish and n-3 fatty acids for the prevention of fatal coronary heart disease and sudden cardiac death." Am J Clin Nutr, 87:1991S-6S (2008).

Mozaffarian, D., et al., "Dietary fish and ω-3 fatty acid consumption and heart rate variability in US adults." Circulation, 117:1130-1137 (2008).

Naba, H., et al., "Improving effect of ethyl eicosapentanoate on statin-induced rhabdomyolysis in Eisai hyperbilirubinemic rats." Biochemical and Biophysical Research Communications, 340:215-220 (2006).

Nakamura, et al., "Effects of Eicosapentaenoic Acids on Remnant-like Particles, Cholesterol Concentrations and Plasma Fatty Acid Composition in Patients with Diabetes Mellitus." in vivo 12: 311-314 (1998).

Nakamura, H., et al., "Evaluation of ethyl icosapentate in the treatment of hypercholesterolemia in kidney transplant recipients." Transplantation Proceedings, 30:3047-3048 (1998).

Nakamura, N., et al., "Joint effects of HMG-CoA reductase inhibitors and eicosapentaenoic acids on serum lipid profile and plasma fatty acid concentrations in patients with hyperlipidemia", International Journal of Clinical and Laboratory Research, Springer, Berlin, DE LNKD-DOI: 10.1007/S005990050057, vol. 29, No. 1, Mar. 1, 1999, pp. 22-25.

Nambi, V., et al., "Combination therapy with statins and omega-3 fatty acids." Am J Cardiol 98:34i-38i (2006).

Nasa, et al., "Long-Term Supplementation With Eicosapentaenoic Acid Salvages Cardiomyocytes From Hypoxia/Reoxygenation-Induced Injury in Rats Fed With Fish-Oil-Deprived Diet," Jpn. J. Pharmacol. 77, 137-146 (1998).

Nattel, S., et al., "Atrial remodeling and atrial fibrillation: Mechanisms and implications." Circ Arrhythmia Electrophysiol, 1:62-73 (2008).

Negre-Salvayre, A., et al., "Advanced lipid peroxidation end products in oxidative damage to proteins. Potential role in diseases and therapeutic prospects for the inhibitors." British Journal of Pharmacology 153:6-20 (2008).

Nelson, G. J., et al., "The Effect of Dietary Docosahexaenoic Acid on Plasma Lipoproteins, and Tissue Fatty Acids Composition in Humans", Lipids, AOCS Press, 32(11):1137-1146, 1997.

Nemets, B., "Addition of Omega-3 Fatty Acid to Maintenance Medication Treatment for Recurrent Unipolar Depressive Disorder" Am J Psychiatry, 159(3):477-479 (Mar. 2002).

Nenseter, MS et al., "Effect of dietary supplementation with n-3 polyunsaturated fatty acids on physical properties and metabolism of low density lipoprotein in humans," Arterioscler. Thromb. Vasc. Biol. 1992; 12;369-379.

Nestel, et al., "The n-3 fatty acids eicosapentaenoic acid and docosahexaenoic acid increase systemic arterial compliance in humans," Am J Clin Nutr 2002; 76:326-30.

Nestel, P.J., "Effects of N-3 fatty acids on lipid metabolism." Ann Rev Nutr. 1990;10:149-167.

Nishikawa M. et al., "Effects of Eicosapentaenoic acid (EPA) on prostacyclin production in diabetics. GC/MS analysis of PG12 and PG13 levels" Methods Find Exp Clin Pharmacol. 19(6):429-33 (Jul.-Aug. 1997).

Nobukata, H., et al., "Age-related changes in coagulation, fibrinolysis, and platelet aggregation in male WBN/Kob rats." Thrombosis Research 98: 507-516 (2000).

Nobukata, H., et al., "Long-term administration of highly purified eicosapentaenoic acid ethyl ester prevents diabetes and abnormalities of blood coagulation in male WBN/Kob rats." Metabolism, 49(12): 912-919 (2000).

Nobukata, H., et al., "Long-term administration of highly purified eicosapentaenoic acid ethyl ester improves the dysfunction of vascular endothelial and smooth muscle cells in male WBN/Kob rats." Metabolism, 49(12): 1588-1591 (2000).

(56) References Cited

OTHER PUBLICATIONS

Nourooz-Zadeh, J., et al., "Urinary 8-epi-PGF2α and its endogenous β-oxidation products (2,3-dinor and 2,3-dinor-5,6-dihydro) as biomarkers of total body oxidative stress." Biochemical and Biophysical Research Communications 330:731-736 (2005).

Nozaki S. et al., "Effects of purified Eicosapentaenoic acid ethyl ester on plasma lipoproteins in primary hypercholesterolemia" Int J Vitam Nutr Res. 62(3):256-60 (1992).

O'Donnell, C.J., et al., "Leukocyte telomere length and carotid artery intimal medial thickness—the Framingham heart study." Arteriosclerosis, Thrombosis, and Vascular Biology.28:1165-1171 (2008).

Obata, et al., (1999) Eicosapentaenoic acid inhibits prostaglandin $D_2$ generation by inhibiting cyclo-oxygenase in cultured human mast cells. Clin. & Experimental Allergy 29: 1129-1135.

Oh, Robert C et al., Management of Hypertriglyceridemia, American Family Physician, May 1, 2007, LNKD-PUBMED: 17508532, vol. 75, No. 9, pp. 1365-1371.

Okuda, Y., et al., (1997) Eicosapentaenoic acid enhances nitric oxide production by cultured human endothelial cells. Biochem. Biophys. Res. Commun. 232: 487-491 (1997).

Okuda, Y., et al., "Long-term effects of eicosapentaenoic acid on diabetic peripheral neuropathy and serum lipids in patients with type II diabetes mellitus." Journal of Diabetes and Its Complications 10:280-287 (1996).

Okumura, T., et al., "Eicosapentaenoic acid improves endothelial function in hypertriglyceridemic subjects despite increased lipid oxidizability." Am J Med Sci 324(5):247-253 (2002).

Oliw, E.H., et al., "Biosynthesis of prostaglandins from 17(18)epoxy-eicosatetraenoic acid, a cytochrome P-450 metabolite of eicosapentaenoic acid." Biochimica el Biophysica Acta, 1126 (1992) 261-268.

Ona, V.O., et al., Nature, vol. 399, "Inhibition of caspase-1 slows disease progression in a mouse model of Huntington's disease," pp. 263-267, May 20, 1999.

Ozawa A, Nakamura E, Jinbo H. Fujita T, Hirai A, Terano T, Hamazaki T et al. "Measurement of higher lipids in the fractions of human red blood cell membranes, blood platelets and plasma, using thin layer chromatography and gas chromatography," Bunseki Kagaku 1982; 32:174-8.

Park, Y., et al., "Omega-3 fatty acid supplementation accelerates chylomicron triglyceride clearance." J. Lipid Res. 44:455-463 (2003).

Pedersen, T., et al., "Randomised trial of cholesterol lowering in 4444 patients with coronary heart disease: the Scandinavian Simvastation Survival Study (4S)", The Lancet, No. 19, 1994, vol. 344, 8934, p. 1383-1389.

Peet, M., et al., "A Dose-Ranging Study of the Effects of Ethyl-Eicosapentaenoate in Patients with Ongoing Depression Despite Apparently Adequate Treatment with Standard Drugs", Arch Gen Psychiatry, 59:913-919, (Oct. 2002).

Peet, M., et al., Phospholipid Spectrum Disorder in Psychiatry pp. 1-19, 1999.

Piccini, Monica, et al., Genomics, vol. 47, "FACL4, a new gene encoding long-chain acyl-CoA synthetase 4, is deleted in a family with Alport syndrome, elliptocytosis, and mental retardation," pp. 350-358, 1998.

Pike, N., "Flushing out the role of GPR109A (HM74a) in the clinical efficacy of nicotinic acid," The Journal of Clinical Investigation, vol. 115, No. 12, Dec. 2005, pp. 3400-3403.

Pownall, H.J., et al., "Correlation of serum triglyceride and its reduction by ω-3 fatty acids with lipid transfer activity and the neutral lipid compositions of high-density and low-density lipoproteins." Atherosclerosis 143:285-297 (1999).

Press Release from Mochida Pharmaceutical Col., Ltd.: Conclusion of Distributorship Agreement Concerning Switch-OTC Drug for Hyperlipidemia Treatment, Epadel, published Apr. 30, 2009.

Press Release: Amarin Corporation Says Huntington's Disease Drug Failed in Trials, http://www.fiercebiotech.com/node/6607/print (Apr. 24, 2007) Printed on Aug. 22, 2008.

Product brochure: "PLUSEPA® "Super Critically" Different from Other Omega-3 Fish Oil Supplements for Depression and ADHD," by Minami Nutrition (Apr. 2009, pp. 1-6).

Puri, B., et al., "Eicosapentaenoic Acid in Treatment-Resistant Depression Associated with Symptom Remission, Structural Brain Changes and Reduced Neuronal Phospholipid Turnover," Int J Clinical Practice 2001; 55:560-563.

Puri, B., et al., Archives of General Psychiatry, No. 55, "Sustained remission of positive and negative symptoms of schizophrenia following treatment with eicosapentaenoic acid," pp. 188-189, 1998.

Puri, B.K., et al., "Ethyl-EPA in Huntington Disease: A Double-Blind, Randomized, Placebo-Controlled Trial", Neurology 65:286-292, (2005).

Qi, K., et al., "Omega-3 fatty acid containing diets decrease plasma triglyceride concentrations in mice by reducing endogenous triglyceride synthesis and enhancing the blood clearance of triglyceride-rich particles." Clinical Nutrition 27(8):424-430 (2008).

Raitt, M.H., et al., "Fish oil supplementation and risk of ventricular tachycardia and ventricular fibrillation in patients with implantable defibrillators—a randomized controlled trial." JAMA. 293(23):2884-2891 (2005).

Rambjor, Gro S., et al., "Eicosapentaenoic Acid is Primarily Responsible for Hypotrigylceridemic Effect of Fish Oil in Humans", Fatty Acids and Lipids from Cell Biology to Human Disease: Proceedings of the $2^{nd}$ international Congress of the ISSFAL (International Society for the Study of Fatty Acids and Lipids, AOCS Press, 31:S-45-S-49, 1996.

Reiffel, J.A., et al., "Antiarrhythmic effects of omega-3 fatty acids." Am J Cardiol 98:50i-60i (2006).

Riediger, N.D., et al., "A systemic review of the roles of n-3 fatty acids in health and disease." J Am Diet Assoc. 109:668-679. (2009).

Risé, P., et al., "Effects of simvastatin on the metabolism of polyunsaturated fatty acids and on glycerolipid, cholesterol, and de novo lipid synthesis in THP-1 cells." J. Lipid Res. 38:1299-1307 (1997).

Roach, P.D., et al., "The effects of dietary fish oil on hepatic high density and low density lipoprotein receptor activities in the rat." FEBS Lett. 1987;222: 159-162.

Robinson, J.G., et al., "Meta-analysis of the relationship between non-high-density lipoprotein cholesterol reduction and coronary heart risk." J Am Coll Cardiol. 2009;53: 316-322.

Roche, H.M., et al., "Effect of long-chain n-3 polyunsaturated fatty acids on fasting and postprandial triacylglycerol metabolism." Am J Clin Nutr 71:232S-7S (2000).

Roche, H.M., et al., "Long-chain n-3 polyunsaturated fatty acids and triacylglycerol metabolism in the postprandial state." Lipids 34: S259-S265 (1999).

Rogers, P. J., "No effect of n-3 long-chain polyunsaturated fatty acid (EPA and DHA) supplementation on depressed mood and cognitive function: a randomised controlled trial" British Journal of Nutrition, 99:421-431, (2008).

Rodriguez, Y., et al., "Long-chain ω6 polyunsaturated fatty acids in erythrocyte phospholipids are associated with insulin resistance in non-obese type 2 diabetics." Clinica Chimica Acta 354:195-199 (2005).

Rubins, H.B., et al., (1995). Distribution of lipids in 8,500 men with coronary artery disease: Department of Veterans Affairs HDL Intervention Trial Study Group. Am. J. Cardiol. 75: 1196-1201.

Rubins, H.B., et al., (1999). Gemfibrozil for the prevention of coronary heart disease in men with low levels of high-density lipoprotein cholesterol. Veterans Affairs HDL-C intervention trial study group. N. Eng. J. Med. 341: 410-418.

Ruiz-Narváez, E.A., et al., "Abdominal obesity and hyperglycemia mask the effect of a common APOC3 haplotype on the risk of myocardial infarction." Am J Clin Nutr 87:1932-8 (2008).

Rustan, A.C., et al., "Eicosapentaenoic acid inhibits cholesterol esterification in cultured parenchymal cells and isolated microsomes from rat liver." J. Bio. Chem. 263(17):8126-32 (1988).

Rustan, A.C., et al., "Eicosapentaenoic acid reduces hepatic synthesis and secretion of triacylglycerol by decreasing the activity of acyl-coenzyme A:1,2-diacylglycerol acyltransferase." J. Lipid Res. 29:1417-1426 (1988).

(56) References Cited

OTHER PUBLICATIONS

Rustan, A.C., et al., "Postprandial decrease in plasma unesterified fatty acids during n-3 fatty acid feeding is not caused by accumulation of fatty acids in adipose tissue." Biochimica et Biophysica Acta 1390.245-25 (1998).
Ryan, A.M., et al., "Enteral nutrition enriched with eicosapentaenoic acid (EPA) preserves lean body mass following esophageal cancer surgery: results of a double-blinded randomized controlled trial." Ann Surg 249:355-363 (2009).
Ryan, A.S., et al., "Clinical overview of algal-docosahexaenoic acid: effects on triglyceride levels and other cardiovascular risk factors." Am J Ther. 2009;16:183-192.
Sacks, Frank M., "The apolipoprotein story," Atherosclerosis Supplements 7 (2006) 23-27.
Saito et al., Effects of EPA on coronary artery disease in hypercholesterolemic patients with multiple risk factors: Sub-analysis of primary prevention cases from the Japan EPA Lipid Intervention Study (JELIS), (Atherosclerosis (2008) 200:135-140).
Saito, J., et al., "Mechanisms of enhanced production of PGI2 in cultured rat vascular smooth muscle cells enriched with eicosapentaenoic acid." Atherosclerosis 131: 219-228 (1997).
Samuels, A., et al., Office Practice of Neurology, Chapter 122, Huntington's Disease, pp. 654-655, 1996.
Sanders, et al., "Influence of an algal triacylglycerol containing docosahexaenoic acid (22:6n-3) and docosapentaenoic acid (22:5n-6) on cardiovascular risk factors in healthy men and women," British Journal of Nutrition (2006), 95, 525-531.
Sanders, T.A., et al., "Effect of varying the ratio of n-6 to n-3 fatty acids by increasing the dietary intake of α-linolenic acid, eicosapentaenoic and docosahexaenoic acid, or both on fibrinogen and clotting factors VII and XII in persons aged 45-70 y: the OPTILIP Study." Am J Clin Nutr 84:513-22 (2006).
Sanders, T.A., et al., "Triglyceride-lowering effect of marine polyunsaturates in patients with hypertriglyceridemia." Arterioscler. Thromb. Vasc. Biol. 5:459-465 (1985).
Sanders, T.A.,et al., "Influence of n-3 fatty acids on blood lipids in normal subjects" Journal of Internal Medicine. 225:99-104,1989.
Sasaki, Y.F., et al., "Bio-anticlastogenic effects of unsaturated fatty acids included in fish oil—docosahexaenoic acid, docosapentaenoic acid, and eicosapentaenoic acid—in cultured Chinese hamster cells." Mutation Research, 320: 9-22 (1994).
Sato, M., et al., "General Pharmacological Studies on 5 8 11 14 17 Eicosapentaenoic Acid Ethyl Ester EPA-E", Folia Pharmacol JPN, (1989) 94 (1), 35-48.
Satoh, N., et al., "Purified eicosapentaenoic acid reduces small dense LDL, remnant lipoprotein particles, and C-reactive protein in metabolic syndrome." Diabetes Care, 30(1): 144-146 (2007).
Schectman, G & Hiatt, J., (1996). Drug therapy for hypercholesterolemia in patients with cardiovascular disease: factors limiting achievement of lipid goals. Am. J. Med. 100: 197-204.
Schectman, G., et al., "Dietary fish oil decreases low-density-lipoprotein clearance in nonhuman primates." Am J Clin Nutr. 1996;64:215-221.
Schectman, G., et al., "Heterogeneity of Low Density Lipoprotein Responses to Fish-Oil Supplementation in Hypertriglyceridemic Subjects." Arterioscler. Thromb. Vasc. Biol. 9:345-354 (1989).
Schmidt, E.B., et al., "Lipoprotein-associated phospholipase A2 concentrations in plasma are associated with the extent of coronary artery disease and correlate to adipose tissue levels of marine n-3 fatty acids." Atherosclerosis 196: 420-424 (2008).
Schmitz, G., et al., "The opposing effects of n-3 and n-6 fatty acids." Progress in Lipid Research, 47:147-155 (2008).
Schwarz, S., et al., "Lycopene inhibits disease progression in patients with benign prostate hyperplasia." J. Nutr. 138: 49-53 (2008).
Serhan, C.N., et al., "Resolvins: A family of bioactive products of omega-3 fatty acid transformation circuits initiated by aspirin treatment that counter proinflammation signals." J. Exp. Med. 196:1025-1037 (2002).
Shah, S., et al., "Eicosapentaenoic Acid (EPA) as an Adjunct in the Treatment of Schizophrenia", Schizophrenia Research, vol. 29, No. 1/02, Jan. 1998.
Shan, Z., et al., "A combination study of spin-trapping, LC/ESR and LC/MS on carbon-centered radicals formed from lipoxygenase-catalysed peroxidation of eicosapentaenoic acid." Free Radical Research, 43(1):13-27 (2009).
Shimizu, H., et al., "Long-term effect of eicosapentaenoic acid ethyl (EPA-E) on albuminuria of non-insulin dependent diabetic patients." Diabetes Research and Clinical Practice 28: 35-40 (1995).
Shinozaki K. et al., "The long-term effect of Eicosapentaenoic acid on serum levels of lipoprotein (a) and lipids in patients with vasciular disease" J Atheroscler Thromb. 2(2):207-9 (1996).
Sierra, S., et al., "Dietary eicosapentaenoic acid and docosahexaenoic acid equally incorporate as decosahexaenoic acid but differ in inflammatory effects." Nutrition 24: 245-254 (2008).
Silvers, K. M., et al., "Randomised double-blind placebo-controlled trial of fish oil in the treatment of depression," Prostagandins, Leukotrienes and Essential Fatty Acids. 72:211-218 (2005).
Simoens, C.M., et al., "Inclusion of 10% fish oil in mixed medium-chain triacylglycerol—longchain triacylglycerol emulsions increases plasma triacylglycerol clearance and induces rapid eicosapentaenoic acid (20:5n-3) incorporation into blood cell phospholipids." Am J Clin Nutr 88: 282-8 (2008).
Simon, J.A., et al., "Serum Fatty Acids and the Risk of Coronary Heart Disease", American Journal of Epidemiology, 142(5):469-476, 1995.
Singer, Peter, "Fluvastatin plus fish oil are more effective on cardiovascular risk factors than fluvastatin alone," Letter to the Editor, Prostaglandinis, Leukotrienes and Essential Fatty Acids, vol. 72, pp. 379-380 (2005) Germany.
Singh, R.B., et al., "Randomized, double-blind, placebo-controlled trial of fish oil and mustard oil in patients with suspected acute myocardial infarction: the Indian experiment of infarct survival—4." Cardiovascular Drugs and Therapy 11:485-491 (1997).
Sirtori, C.R., et al., "One-year treatment with ethyl esters of n-3 fatty acids in patients with hypertriglyceridemia and glucose intolerance—Reduced triglyceridemia, total cholesterol and increased HDL-C." Atherosclerosis 137: 419-427 (1998).
Skinner JS, Cooper A, & Feder GS and on behalf of the Guideline Development Group. "Secondary prevention for patients following a myocardial infarction; summary of NICE guidance," Heart 2007; 93:862-864.
Smith et al., Pharmacokinetics and Pharmacodynamics of Epoetin Delta in Two Studies in Health Volunteers and Two Studies in Patients with Chronic Kidney Disease, Clinical Therapeutics/vol. 29, No. 7, 2007, pp. 1368-1380.
Sohma, R., et al., "Protective effect of n-3 polyunsaturated fatty acid on primary culture of rat hepatocytes without glycemic alterations." Journal of Gastroenterology and Hepatology 22: 1965-1970 (2007).
Spector, A.A., "Arachidonic acid cytochrome P450 epoxygenase pathway." Journal of Lipid Research, 50: S52-S56 (2009) (published online on Oct. 23, 2008).
Spector, A.A., et al., "Epoxyeicosatrienoic acids (EETs): metabolism and biochemical function." Progress in Lipid Research 43: 55-90 (2004).
Springer, T.A., "Traffic signals for lymphocyte recirculation and leukocyte emigration: The multistep paradigm." Cell, 76: 301-314 (1994).
Squires et al., Low-Dose, Time-Release Nicotinic Acid: Effects in Selected Patients With Low Concentrations of High-Density Lipoprotein Cholesterol, May Clin Proc 67:855-860, 1992.
Srinivas, et al., "Controlled release of lysozyme from succinylated gelatin microspheres," J. Biomater. Sci., Polymer Ed., vol. 12(2):137-148 (2001).
Stalenhoef, A.F.H., et al., "The effect of concentrated n-3 fatty acids versus gemfibrozil on plasma lipoproteins, low density lipoprotein heterogeneity and oxidizability in patients with hypertrygliceridemia." Atherosclerosis 153: 129-138 (2000).
Stark, K.D. & Holub, B.J., Differential eicosapentaenoic acid elevations and altered cardiovascular disease risk factor responses after supplementation with docosahexaenoic acid in postmenopausal

(56) References Cited

OTHER PUBLICATIONS women receiving and not receiving hormone replacement therapy, Am. J. Clin. Nutr., vol. 79, pp. 765-773 (2004).
Stark, K.D., "The percentage of n-3 highly unsaturated fatty acids in total HUFA as a biomarker for omega-3 fatty acid status in tissues." Lipids 43:45-53 (2008).
Stark, K.D., et al., "Effect of a fish-oil concentrate on serum lipids in postmenopausal women receiving and not receiving hormone replacement therapy in a placebo-controlled, double-blind trial." Am J Clin Nutr 72:389-94 (2000).
Stoll, A.L., et al., Arch. Gen. Psychiatry, vol. 56, "Omega 3 Fatty Acids in Bipolar Disorder", pp. 407-412, May 1999.
Su, K. P., et al. "Omega-3 Fatty Acids in Major Depressive Disorder a Preliminary Double-Blind, Placebo-Controlled Trial" European Neuropsychopharmacology, 13:267-271 (2003).
Sugiyama, E., et al., "Eicosapentaenoic acid lowers plasma and liver cholesterol levels in the presence of peroxisome proliferators-activated receptor alpha." Life Sciences, 83:19-28 (2008).
Superko et al., "Lipid Management to Reduce Cardiovascular Risk: A New Strategy is Required," Circulation 2008, 117:560-568.
Surette, M.E., et al., "Dependence on dietary cholesterol for n-3 polyunsaturated fatty acidinduced changes in plasma cholesterol in the Syrian hamster." J Lipid Res. 1992;33:263-271.
Surette, M.E., et al., "Evidence for mechanisms of the hypotriglyceridemic effect of n-3 polyunsaturated fatty, acids." Biochimica et Biophysic Acta, 1126: 199-205 (1992).
Tamura, et al., "Study of the Clinical Usefulness of Ethyl Icosapentate (MND-21) in Long-Term Treatment of Hyperlipaemic Patients." J Clin Thera & Medicines 1991; 7:1817-1834.
Tanaka, K.T., et al., "Reduction in the recurrence of stroke by eicosapentaenoic acid for hypercholesterolemic patients—Subanalysis of the JELIS trial." Stroke, 39(7):2052-8 (2008).
Tatarczyk, et al., "Analysis of long-chain ω-3 fatty acid content in fish-oil supplements," Wien Klin Wochenschr (2007) 119/13-14: 417-422.
Taylor et al., Arterial Biology for the Investigation of the Treatment Effects of Reducing Cholesterol (ARBITER) 2: A Double-Blind, Placebo-Controlled Study of Extended-Release Niacin on Atherosclerosis Progression in Secondary Prevention Patients Treated With Statins, Circulation 2004;110;3512-3517.
Tedgui, A., et al., "Anti-inflammatory mechanisms in the vascular wall." Circ. Res. 88:877-887 (2001).
Terano, et al., "Effect of Oral Administration of Highly Purified Eicosapentaenoic Acid on Platelet Function, Blood Vicosity and Red Cell Deformability in Healthy Human Subjects," Atherosclerosis, 46 (1983) 321-331.
Theilla, M., et al., "A diet enriched in eicosapentanoic acid, gamma-linolenic acid and antioxidants in the prevention of new pressure ulcer formation in critically ill patients with acute lung injury: A randomized, prospective, controlled study." Clinical Nutrition 26: 752-757 (2007).
Thies, F., et al., "Association of n-3 polyunsaturated fatty acids with stability of atherosclerotic plaques: a randomised controlled trial." Lancet 361: 477-85 (2003).
Thies, F., et al., "Dietary supplementation with eicosapentaenoic acid, but not with other long-chain n-3 or n-6 polyunsaturated fatty acids, decreases natural killer cell activity in healthy subjects aged >55 y." Am J Clin Nutr 73:539-48 (2001).
Tirosh et al., "Changes in Triglyceride Levels and Risk for Coronary Heart Disease in Young Men," 2007 American College of Physicians, pp. 377-385.
Torrejon, C. et al., "n-3 Fatty acids and cardiovascular disease: Actions and molecular mechanisms," Prostaglandins Leukotrienes & Essent. Fatty Acids (2007), doi:10.1016/j.plefa.2007.10.014.
TREND-HD Investigators, Randomized controlled trial of ethyl-eicosapentaenoic acid in Huntington disease: the TREND-HD study, Arch Neurol. 2008, vol. 65(12): 1582-9.
Tsuruta K., et al.,"Effects of purified eicosapentaenoate ethyl ester on fibriolytic capacity in patients with stable coronary artery disease and lower extremity ischaemia" Coron Artery Dis. 7(11):837-42 (Nov. 1996).
Tungsiripat, et al., "Dyslipidemia in HIV patients," Cleveland Clinic Journal of Medicine, v. 72, No. 12, Dec. 2005.
Ullian, M.E., "Fatty acid inhibition of angiotensin II-stimulated inositol phosphates in smooth muscle cells." Am J Physiol Heart Circ Physiol (Nov. 1996).
Urakaze, M., et al., "Infusion of emulsified trieicosapentaenoylglycerol into rabbits. The effects on platelet aggregation, polymorphonuclear leukocyte adhesion, and fatty acid composition in plasma and platelet phosphollpids", Thromb. Res. (1986) 44(5), pp. 673-682.
US Food and Drug Administration and Dept of Health and Human Services. Substances affirmed as generally recognized as safe: Menhaden Oil. Fed Register 1997; 62:30751-30757.
Vaddadi, K. S., et al., "A Randomised, Placebo-Controlled, Double-Blind Study of Treatment of Huntington's Disease with Unsaturated Fatty Acids" Clinical Neuroscience and Neuropathology, 13(1):29-33 (Jan. 2002).
Van der Steeg, W.A., et al., "High-density lipoprotein cholesterol, high-density lipoprotein particle size, and apolipoprotein A-I: Significance for cardiovascular risk—the IDEAL and EPIC-Norfolk studies." J. Am. Coll. Cardiol. 51;634-642 (2008).
Vasudevan et al., "Effective Use of Combination of Lipid Therapy", Curr. Atheroscl. Rep., vol. 8, pp. 76-84 (2006).
Vedin, I., et al., "Effects of docosahexaenoic acid—rich n-3 fatty acid supplementation on cytokine release from blood mononuclear leukocytes: the OmegAD study." Am J Clin Nutr 87:1616-22 (2008).
Vidgren, H.M., et al., "Incorporation of n-3 fatty acids into plasma lipid fractions, and erythrocyte membranes and platelets during dietary supplementation with fish, fish oil, and docosahexaenoic acid-rich oil among healthy young men." Lipids 32: 697-705 (1997).
Volcik, K.A., et al., "Peroxisome proliferator—activated receptor agenetic variation interacts with n-6 and long-chain n-3 fatty acid intake to affect total cholesterol and LDL-cholesterol concentrations in the Atherosclerosis Risk in Communities Study." Am J Clin Nutr 87:1926-31 (2008).
Von Schacky, C., "A review of omega-3 ethyl esters for cardiovascular prevention and treatment of increased blood triglyceride levels." Vascular Health and Risk Management 2(3): 251-262 (2006).
Von Schacky, C., et al., "The Effect of Dietary ω-3 Fatty Acids on Cornoray Atherosclerosis: A Randomized, Double-Blind, Placebo-Controlled Trial", American College of Physicians—American Society of Internal Medicine, 130(7):554-562, 1999.
Wada, M., et al., "Enzymes and receptors of prostaglandin pathways with arachidonic acid-derived versus eicosapentaenoic acid-derived substrates and products." J. Biol. Chem. 282(31): 22254-22266 (2007).
Walldius, G., et al., "Editorial: Rationale for using apolipoprotein B and apolipoprotein A-I as indicators of cardiac risk and as targets for lipid-lowering therapy." European Heart Journal 26, 210-212 (2005).
Wander, R.C., et al., "Influence of long.chain polyunsaturated fatty acids on oxidation of low density lipoprotein." Prostaglandins, Leukotrienes and Essential Fatty Acids 59(2):143-151 (1998).
Wang, C., et al., "n-3 Fatty acids from fish or fish-oil supplements, but not α-linolenic acid, benefit cardiovascular disease outcomes in primary- and secondary-prevention studies: a systematic review." Am J Clin Nutr 84:5-17 (2006).
Wang, L., et al., "Triglyceride-rich lipoprotein lipolysis releases neutral and oxidized FFAs that induce endothelial cell inflammation." J. Lipid Res. 50:204-213 (2009).
Warren, S.T., Science, vol. 271, "The Expanding World of Trinucleotide Repeats", pp. 1374-1375, Mar. 8, 1996.
Watanabe, I., et al., "Usefulness of EPA-E (eicosapentaenoic acid ethyl ester) in preventing neointimal formation after vascular injury", Kokyu to Junkan (1994), 42(7), pp. 673-677.

(56) References Cited

OTHER PUBLICATIONS

Weaver, K.L., et al., "Effect of Dietary Fatty Acids on Inflammatory Gene Expression in Healthy Humans." J. Biol. Chem., 284(23): 15400-15407 (2009) (published online Apr. 9, 2009.).
Weber, P., "Triglyceride-lowering effect of n-3 long chain polyunsaturated fatty acid: eicosapentaenoic acid vs. docosahexaenoic acid." Lipids 34: S269 (1999).
Westerveld H.T. et al., "Effects of low-dose EPA-E on glycemic control, lipid profile, lipoprotein(a), platelet aggretation, viscosity, and platelet and vessel wall interaction in NIDDM" Diabetes Care 16(5):683-8 (May 1993).
Westphal, S., et al., "Postprandial chylomicrons and VLDLs in severe hypertriacylglycerolemia are lowered more effectively than are chylomicron remnants after treatment with n23 fatty acids." Am J Clin Nutr 71:914-20 (2000).
Whelan, J., et al., "Evidence that dietary arachidonic acid increases circulating triglycerides." Lipids 30, 425-429 (1995).
Wierzbicki, a.S., "Editorial: Newer, lower, better? Lipid drugs and cardiovascular disease—the continuing story." Int J Clin Pract, 61(7):1064-1067 (2007).
Wierzbicki, A.S., "Editorial: Raising HDL-C: back to the future?" Int J Clin Pract, 61(7): 1069-1071 (2007).
Willumsen, N. et al., Biochimica et Biophysica Acta. vol. 1369, "On the effect of 2-deuterium- and 2-methyl-eicosapentaenoic acid derivatives on triglycerides, peroxisomal beta-oxidation and platelet aggregation in rats," pp. 193-203, 1998.
Willumsen, N., et al., "Eicosapentaenoic acid, but not docosahexaenoic acid, increased, mitochondrial fatty acid oxidation and upregulates 2,3-dienoyl-CoA reductase gene expression in rats." Lipids, 31:579-592 (1996).
Wilson Omega 3 fish oil: EPA versus DHA (Dietivity.com, 2006, 1-16).
Wilt, V.M. & Gumm, J.G. (1997). "Isolated" low high-density lipoprotein cholesterol. Ann. Pharmacol. 31: 89-97.
Wink et al., Effect of very-low-dose niacin on high-density lipoprotein in patients undergoing long-term statin therapy, Am Heart J 2002;143:514-8.
Wojenski, C.M., et al., "Eicosapentaenoic acid ethyl ester as an antithrombotic agent: comparison to an extract of fish oil." Biochimica et Biophysica Acta. 1081:33-38 (1991).
Wong, S.H., et al., "Effects of eicosapentaenoic and docosahexaenoic acids on Apoprotein B mRNA and secretion of very low density lipoprotein in HepG2 cells." Arterioscler. Thromb. Vasc. Biol. 9;836-841 (1989).
Woodman, R. J., et al., "Effects of Purified Eicoaspentaenoic and Docosahexaenoic Acids on Glycemic Control, Blood Pressure, and Serum Lipids in Type 2 Diabetic Patients with Treated Hypertension" The American Journal of Clinical Nutrition: Official Journal of the American Society for Clinical Nutrition, Inc. 76(5):1007-1015 (Nov. 1, 2002).
Woodman, R.J., et al., "Effects of purified eicosapentaenoic acid and docosahexaenoic acid on platelet, fibrinolytic and vascular function in hypertensive type 2 diabetic patients." Atherosclerosis 166: 85-93 (2003).
Wu, W.H., et al., "Effects of docosahexaenoic acid supplementation on blood lipids, estrogen metabolism, and in vivo oxidative stress in postmenopausal vegetarian women." Eur J Clin Nutr. 2006;60:386-392.
Xiao, Y.F., et al., "Inhibitory effect of n-3 fish oil fatty acids on cardiac $Na^+/Ca^{2+}$ exchange currents in HEK293t cells." Biochemical and Biophysical Research Communications 321: 116-123 (2004).
Xiao, Y-F., et al., "Blocking effects of polyunsaturated fatty acids on $Na^+$ channels of neonatal rat ventricular myocytes." Proc. Natl. Acad. Sci. 92: 11000-11004 (1995).
Xiao, Y-F., et al., "Fatty acids suppress voltage-gated $Na^+$ currents in HEK293t cells transfected with the a-subunit of the human cardiac $Na^+$ channel." Proc. Natl. Acad. Sci. 95: 2680-2685 (1998).
Xydakis, A M et al., "Combination therapy for combined dyslipidemia," American Journal of Cardiology, 20021120 US, vol. 90, No. 10 Suppl. 2, Nov. 20, 2002, p. 21K-29K.
Yamamoto, H. et al., Improvement of coronary vasomotion with Eicosapentaenoic acid does not inhibit acetylcholine-induced coronary vasospasm in patients with variant angina: Jpn Cir J. 59(9):608-16 (Sep. 1995).
Yamamoto, K., et al., "4-Hydroxydocosahexaenoic acid, a potent Peroxisome Proliferator-Activated Receptor C agonist alleviates the symptoms of DSS-induced colitis." Biochemical and Biophysical Research Communications 367: 566-572 (2008).
Yamashita, Atsushi, et al., J. Biochem., vol. 122, No. 1, "Acyltransferases and Transaclyases Involved in Fatty Acid Remoding of Phospholipids and Metabolism of Bioactive Lipids in Mammalian Cells", pp. 1-16, 1997.
Yamashita, N., et al., "Inhibition of natural killer cell activity of human lymphocytes by eicosapentaenoic acid." Biochem. Biophys. Res. Comm. 138(3): 1058-1067 (1986).
Yamazaki, et. al., "Dissolution tests by RDC method for soft gelatin capsules containing ethyl icosapentate,", Pharm. Tech. Japan, vol. 15, No. 4, pp. 595-603 (1999). Abstract.
Yamazaki, K., et al., "Changes in fatty acid composition in rat blood and organs after infusion of eicosapentaenoic acid ethyl ester", Biochim. Biophys. Acta (1992), 1128(1), 35-43.
Yang, S.P., et al., "Eicosapentaenoic acid attenuates vascular endothelial growth factor-induced proliferation via inhibiting Flk-1 receptor expression in bovine carotid artery endothelial cells." J. Cell. Physio. 176:342-349 (1998).
Yano T, Mizuguchi K, Takasugi K, Tanaka Y, Sato M. "Effects of ethyl all-cis-5,8,11,14,17-icosapentaenoate on low density lipoprotein in rabbits," Yakugaku Zasshi 1995; 115:843-51.
Yano, T., et al., "Effects of ethyl-all-cis-5,8,11,14,17-icosapentaenoate (EPA-E), pravastatin and their combination on serum lipids and intimal thickening of cuff-sheathed carotid artery in rabbits." Life Sciences, 61(20):2007-2015 (1997).
Yerram, N.R., et al., "Eicosapentaenoic acid metabolism in brain microvessel endothelium: effect on prostaglandin formation." J. Lipid Res.30:1747-1757 (1989).
Yokoyama et al., "Effects of eicosapentaenoic acid on major coronary events in hypercholesterolaemic patients (JELIS): a randomized open-label, blinded endpoint analysis", Lancet, vol. 369, pp. 1090-1098 (2007).
Yoshimura, T., et al., Effects of highly purified eicosapentaenoic acid on plasma beta thromboglobulin level and vascular reactivity to angiotensin II, Artery (1987) 14(5) pp. 295-303.
Zaima, N., et al., "Trans geometric isomers of EPA decrease LXRa-induced cellular triacylglycerol via suppression of SREBP-1c and PGC-1β." J. Lipid Res. 47: 2712-2717 (2006).
Zanarini, et al., "Omega-3 Fatty Acid Treatment of Women with Borderline Personality Disorder: A Double-Blind, Placebo-Controlled Pilot Study," Am J Psychiatry 2003; 160:167-169.
Zhang, M., et al., "Effects of eicosapentaenoic acid on the early stage of type 2 diabetic nephropathy in KKAy/Ta mice: involvement of anti-inflammation and antioxidative stress." Metabolism Clinical and Experimental 55:1590-1598 (2006).
Zhang, Y.W., et al., "Inhibitory effects of eicosapentaenoic acid (EPA) on the hypoxia/reoxygenation-induced tyrosine kinase activation in cultured human umbilical vein endothelial cells." Prostaglandins, Leukotrienes and Essential FattyAcids 67(4):253-261 (2002).
Zhang, Y.W., et al., "Pretreatment with eicosapentaenoic acid prevented hypoxia/reoxygenation-induced abnormality in endothelial gap junctional intercellular communication through inhibiting the tyrosine kinase activity." Prostaglandins, Leukotrienes and Essential Fatty Acids 61(1): 33-40 (1999).
Zhao, G. et al., "Dietary α-linolenic acid inhibits proinflammatory cytokine production by peripheral blood mononuclear cells in hypercholesterolemic subjects." Am J Clin Nutr 85:385-91 (2007).
Zhao, G., et al., "Dietary α-linolenic acid reduces inflammatory and lipid cardiovascular risk factors in hypercholesterolemic men and women." J. Nutr. 134: 2991-2997 (2004).

(56) References Cited

OTHER PUBLICATIONS

Ziegler, D., et al., "Treatment of symptomatic diabetic polyneuropathy with the antioxidant α-lipoic acid: A 7-month multicenter randomized controlled trial (ALADIN III Study)." Diabetes Care 22:1296-1301 (1999).

Zuijdgeest-van Leeuwen, et al., "N-3 Fatty Acids Administered as Triacylglycerols or as Ethyl Esters Have Different Effects on Serum Lipid Concentrations in Healthy Subjects," N-3 Fatty Acids, Lipid Metabolism and Cancer, Feb. 2000, pp. 89-100.

Zuijdgeest-van Leeuwen, S.D., et al., "Incorporation and washout of orally administered n-3 fatty acid ethyl esters in different plasma lipid fractions." British Journal of Nutrition 82:481-488 (1999).

Zuijdgeest-van Leeuwen, SD, et al., "Eicosapentaenoic acid inhibits lipolysis in weight-losing cancer patients as well as in healthy volunteers," Eur J Gastroenterol & Hepatol 1998; 10(12):A67.

U.S. Appl. No. 13/614,111, filed Sep. 13, 2012.
U.S. Appl. No. 13/614,129, filed Sep. 13, 2012.
U.S. Appl. No. 13/614,146, filed Sep. 13, 2012.
U.S. Appl. No. 13/685,281, filed Nov. 26, 2012.
U.S. Appl. No. 13/685,291, filed Nov. 26, 2012.
U.S. Appl. No. 13/768,869, filed Feb. 15, 2013.
U.S. Appl. No. 13/768,897, filed Feb. 15, 2013.
U.S. Appl. No. 13/768,906, filed Feb. 15, 2013.
U.S. Appl. No. 13/777,398, filed Feb. 26, 2013.

* cited by examiner

STABLE PHARMACEUTICAL COMPOSITION AND METHODS OF USING SAME

PRIORITY CLAIM

This application claims priority from co-pending U.S. application Ser. No. 13/685,291 filed on Nov. 26, 2012, which claims priority to U.S. application Ser. No. 13/614,111 filed Sep. 13, 2012, which claims priority to U.S. application Ser. No. 13/458,496 filed Apr. 27, 2012, which claims priority from U.S. application Ser. No. 12/769,885 filed Apr. 29, 2010, which claims priority to U.S. provisional patent application 61/173,763, filed Apr. 29, 2009, the entireties of each of which are hereby incorporated by reference herein.

BACKGROUND

Mixed omega-3 fatty acid esters are typically encapsulated in type 2a gelatin capsules containing gelatin (~43.4%), glycerol (~20%) and water (~36.6%) and do not experience stability problems throughout their shelf life. While chemically modified gelatins such as succinated/succinylated gelatin have been used to encapsulate reactive fill ingredients, such gelatin is not approved for use in the U.S. and other markets.

SUMMARY

We have unexpectedly found that high purity eicosapentaenoic acid (EPA) is more susceptible to oxidative degradation than mixed omega-3-acid ethyl esters. In various embodiments, the invention provides pharmaceutical compositions comprising a fatty acid or a derivative thereof in a capsule shell that resists, hinders, attenuates, or prevents oxidation of the fatty acid or fatty acid derivative, for example to a greater extent than is provided by a standard type IIa capsule shell. In a related embodiment, the fatty acid comprises eicosapentaenoic acid (EPA) or a derivative of EPA, for example ethyl eicosapentaenoate (ethyl-EPA or E-EPA). In another embodiment, the fatty acid comprises ultra-pure EPA.

In one embodiment, the invention provides a pharmaceutical composition comprising ultra-pure EPA encapsulated in a capsule shell, where the ultra-pure EPA has a baseline peroxide value not greater than about 5 meq/mg and upon storage of the composition at 23° C. and 50% RH for a period of time, that ultra-pure EPA has a second peroxide value not greater than about 20 meq/mg.

In other embodiments, the invention provides a pharmaceutical composition comprising EPA (e.g. E-EPA or ultra pure E-EPA) encapsulated in a capsule shell comprising a film forming material and a hygroscopic plasticizer, wherein the weight ratio of film-forming material to hygroscopic plasticizer is not less than about 2.5:1. Further, the capsule shell can optionally comprise a non-hygroscopic plasticizer. In one embodiment, the capsule contains no chemically modified gelatin, for example succinated or succinylated gelatin.

In still other embodiments, the present invention provides methods of treating or preventing a cardiovascular-related disease using compositions as described herein.

These and other embodiments of the present invention will be disclosed in further detail herein below.

DETAILED DESCRIPTION

Figure 1:
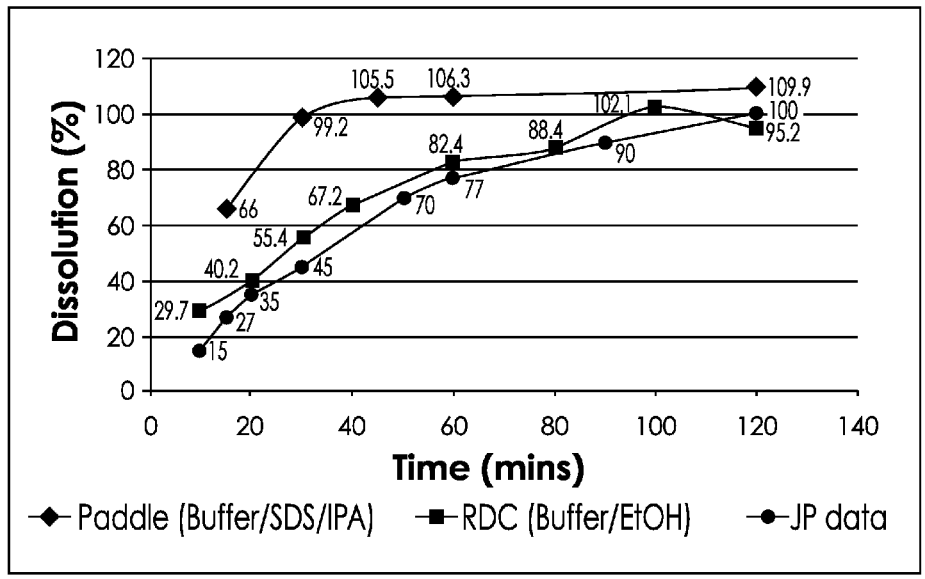
FIG. 1 shows dissolution profile of an inventive capsule composition containing ~500 mg E-EPA versus a composition comprising EPA in a succinated gelatin capsule.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

Polyunsaturated Fatty Acids

In one embodiment, compositions of the invention comprise a polyunsaturated fatty acid as an active ingredient. In another embodiment, compositions of the invention comprise EPA as an active ingredient. The term "EPA" as used herein refers to eicosapentaenoic acid (e.g. eicosa-5,8,11,14,17-pentaenoic acid) and/or a pharmaceutically acceptable ester, derivative, conjugate or salt thereof, or mixtures of any of the foregoing.

In one embodiment, the EPA comprises all-cis eicosa-5,8,11,14,17-pentaenoic acid. In another embodiment, the EPA is in the form of an eicosapentaenoic acid ester. In another embodiment, the EPA comprises a $C_1$-$C_5$ alkyl ester of EPA. In another embodiment, the EPA comprises eicosapentaenoic acid ethyl ester, eicosapentaenoic acid methyl ester, eicosapentaenoic acid propyl ester, or eicosapentaenoic acid butyl ester. In still another embodiment, the EPA comprises all-cis eicosa-5,8,11,14,17-pentaenoic acid ethyl ester.

In still other embodiments, the EPA comprises ethyl-EPA, lithium EPA, mono, di- or triglyceride EPA or any other ester or salt of EPA, or the free acid form of EPA. The EPA may also be in the form of a 2-substituted derivative or other derivative which slows down its rate of oxidation but does not otherwise change its biological action to any substantial degree.

The term "pharmaceutically acceptable" in the present context means that the substance in question does not produce unacceptable toxicity to the subject or interaction with other components of the composition.

In one embodiment, EPA present in a composition of the invention comprises ultra-pure EPA. The term "ultra-pure" as used herein with respect to EPA refers to a composition comprising at least 96% by weight EPA (as the term "EPA" is defined and exemplified herein). Ultra-pure EPA can comprise even higher purity EPA, for example at least 97% by weight EPA or at least 98% by weight EPA, wherein the EPA is any form of EPA as set forth herein. Ultra-pure EPA can further be defined (e.g. impurity profile) by any of the description of EPA provided herein.

In other embodiments, EPA is present in a composition of the invention in an amount of about 50 mg to about 5000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, or about 2500 mg.

In various embodiments, one or more antioxidants can be present in the EPA (e.g. E-EPA or ultra pure E-EPA). Non-limiting examples of suitable antioxidants include tocopherol, lecithin, citric acid and/or ascorbic acid. One or more antioxidants, if desired, are typically present in the EPA in an amount of about 0.01% to about 0.1%, by weight, or about 0.025% to about 0.05%, by weight.

In one embodiment, a composition of the invention contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight of total fatty acids, docosahexaenoic acid or derivative thereof such as E-DHA, if any. In another embodiment, a composition of the invention contains substantially no docosahexaenoic acid or derivative thereof such as E-DHA. In still another embodiment, a composition of the invention contains no docosahexaenoic acid or E-DHA.

In another embodiment, EPA represents at least about 60%, at least about 70%, at least about 80%, at least about 90%, at least about 95%, at least about 97%, at least about 98%, at least about 99%, or 100%, by weight, of all fatty acids present in a composition of the invention.

In another embodiment, a composition of the invention contains less than 30%, less than 20%, less than 10%, less than 9%, less than 8%, less than 7%, less than 6%, less than 5%, less than 4%, less than 3%, less than 2%, less than 1%, less than 0.5% or less than 0.25%, by weight of the total composition or by weight of the total fatty acid content, of any fatty acid other than EPA, or derivative thereof. Illustrative examples of a "fatty acid other than EPA" include linolenic acid (LA) or derivative thereof such as ethyl-linolenic acid, arachidonic acid (AA) or derivative thereof such as ethyl-AA, docosahexaenoic acid (DHA) or derivative thereof such as ethyl-DHA, alpha-linolenic acid (ALA) or derivative thereof such as ethyl-ALA, stearadonic acid (STA) or derivative thereof such as ethyl-SA, eicosatrienoic acid (ETA) or derivative thereof such as ethyl-ETA and/or docosapentaenoic acid (DPA) or derivative thereof such as ethyl-DPA.

In another embodiment, a composition of the invention has one or more of the following features: (a) eicosapentaenoic acid ethyl ester represents at least 96%, at least 97%, or at least 98%, by weight, of all fatty acids present in the composition; (b) the composition contains not more than 4%, not more than 3%, or not more than 2%, by weight, of total fatty acids other than eicosapentaenoic acid ethyl ester; (c) the composition contains not more than 0.6%, 0.5%, or 0.4% of any individual fatty acid other than eicosapentaenoic acid ethyl ester; (d) the composition has a refractive index (20° C.) of about 1 to about 2, about 1.2 to about 1.8 or about 1.4 to about 1.5; (e) the composition has a specific gravity (20° C.) of about 0.8 to about 1.0, about 0.85 to about 0.95 or about 0.9 to about 0.92; (f) the composition contains not more than 20 ppm, 15 ppm or 10 ppm heavy metals, (g) the composition contains not more than 5 ppm, 4 ppm, 3 ppm, or 2 ppm arsenic, and/or (h) the composition has a peroxide value not more than 5, 4, 3, or 2.

In another embodiment, a composition useful in accordance with the invention comprises, consists essentially of or consists of at least 95% by weight ethyl eicosapentaenoate (EPA-E), about 0.2% to about 0.5% by weight ethyl octadecatetraenoate (ODTA-E), about 0.05% to about 0.25% by weight ethyl nonaecapentaenoate (NDPA-E), about 0.2% to about 0.45% by weight ethyl arachidonate (AA-E), about 0.3% to about 0.5% by weight ethyl eicosatetraenoate (ETA-E), and about 0.05% to about 0.32% ethyl heneicosapentaenoate (HPA-E). In another embodiment, the composition is present in a capsule shell. In still another embodiment, the capsule shell contains no chemically modified gelatin.

In another embodiment, compositions useful in accordance with the invention comprise, consist essentially of, or consist of at least 95%, 96% or 97%, by weight, ethyl eicosapentaenoate, about 0.2% to about 0.5% by weight ethyl octadecatetraenoate, about 0.05% to about 0.25% by weight ethyl nonaecapentaenoate, about 0.2% to about 0.45% by weight ethyl arachidonate, about 0.3% to about 0.5% by weight ethyl eicosatetraenoate, and about 0.05% to about 0.32% by weight ethyl heneicosapentaenoate. Optionally, the composition contains not more than about 0.06%, about 0.05%, or about 0.04%, by weight, DHA or derivative there of such as ethyl-DHA. In one embodiment the composition contains substantially no or no amount of DHA or derivative there of such as ethyl-DHA. The composition further optionally comprises one or more antioxidants (e.g. tocopherol) in an amount of not more than about 0.5% or not more than 0.05%. In another embodiment, the composition comprises about 0.05% to about 0.4%, for example about 0.2% by weight tocopherol. In another embodiment, about 500 mg to about 1 g of the composition is provided in a capsule shell. In another embodiment, the capsule shell contains no chemically modified gelatin.

In another embodiment, compositions useful in accordance with the invention comprise, consist essentially of, or consist of at least 96% by weight ethyl eicosapentaenoate, about 0.22% to about 0.4% by weight ethyl octadecatetraenoate, about 0.075% to about 0.20% by weight ethyl nonaecapentaenoate, about 0.25% to about 0.40% by weight ethyl arachidonate, about 0.3% to about 0.4% by weight ethyl eicosatetraenoate and about 0.075% to about 0.25% by weight ethyl heneicosapentaenoate. Optionally, the composition contains not more than about 0.06%, about 0.05%, or about 0.04%, by weight, DHA or derivative there of such as ethyl-DHA. In one embodiment the composition contains substantially no or no amount of DHA or derivative there of such as ethyl-DHA. The composition further optionally comprises one or more antioxidants (e.g. tocopherol) in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell. In one embodiment, the dosage form is a gel- or liquid-containing capsule and is packaged in blister packages of about 1 to about 20 capsules per sheet.

In another embodiment, compositions useful in accordance with the invention comprise, consist essentially of or consist of at least 96%, 97% or 98%, by weight, ethyl eicosapentaenoate, about 0.25% to about 0.38% by weight ethyl octadecatetraenoate, about 0.10% to about 0.15% by weight ethyl nonaecapentaenoate, about 0.25% to about 0.35% by weight ethyl arachidonate, about 0.31% to about 0.38% by weight ethyl eicosatetraenoate, and about 0.08% to about 0.20% by weight ethyl heneicosapentaenoate. Optionally, the composition contains not more than about 0.06%, about 0.05%, or about 0.04%, by weight, DHA or derivative there of such as ethyl-DHA. In one embodiment the composition contains substantially no or no amount of DHA or derivative there of such as ethyl-DHA. The composition further optionally comprises one or more antioxidants (e.g. tocopherol) in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell. In another embodiment, the capsule shell contains no chemically modified gelatin.

In various embodiments, the invention provides a polyunsaturated fatty acid such as EPA (e.g. E-EPA or ultra pure E-EPA) encapsulated in a pharmaceutical capsule shell. In one embodiment, the capsule shell resists, hinders, attenuates, or prevents oxidation of the fatty acid or fatty acid derivative. In another embodiment, the capsule shell resists, hinders, attenuates, or prevents oxidation of the polyunsaturated fatty acid or derivative to a greater extent than a standard type IIa gelatin capsule. In another embodiment, the capsule contains no chemically modified gelatin, for example succinated, succinylated, pthalated, carbanylated and/or phenol carbanylated gelatin.

In another embodiment, the invention provides a pharmaceutical composition comprising EPA (e.g. E-EPA or ultra pure E-EPA) encapsulated in a capsule shell as described herein and having a baseline peroxide value not greater than about 10 meq/mg, about 9 meq/mg, about 8 meq/mg, about 7 meq/mg, about 6 meq/mg, about 5 meq/mg, about 4 meq/mg, about 3 meq/mg or about 2 meq/mg, wherein upon storage of the composition at 23° C. and 50% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, the ultra-pure EPA has a second peroxide value not greater than about 25 meq/mg, about 24 meq/mg, about 23 meq/mg, about 22 meq/mg, about 21 meq/mg, about 20 meq/mg, about 19 meq/mg, about 18 meq/mg, about 17 meq/mg, about 16 meq/mg, about 15 meq/mg, about 14 meq/mg, about 13 meq/mg, about 12 meq/mg, about 11 meq/mg, about 10 meq/mg, about 9 meq/mg, about 8 meq/mg, about 7 meq/mg, about 6 meq/mg, about 5 meq/mg, about 4 meq/mg, about 3 meq/mg or about 2 meq/mg.

The "baseline peroxide value" and "second peroxide values" can be measured in any suitable manner, for example by using a U.S. or PhEur or JP compendial method. Typically, a plurality of encapsulated EPA compositions are provided, each composition containing EPA having been encapsulated at substantially the same time. A first sampling of 1 or more capsules from the plurality is provided, the capsules are opened and peroxide value of the EPA is measured substantially immediately thereafter, providing an average baseline peroxide value. At substantially the same time, a second sampling of 1 or more capsules from the plurality are provided and are placed under desired storage conditions for a desired time period. At the end of the desired time period, the capsules are opened and peroxide value of the EPA is measured substantially immediately thereafter, providing an average second peroxide value. The baseline and second peroxide values can then be compared. In one embodiment, the "baseline peroxide value" and "second peroxide value" are determined using a plurality of encapsulated EPA dosage units wherein each dosage unit was encapsulated (i.e. the EPA filled and sealed into capsules) within a same 60 day period, same 30 day period, a same 20 day period, a same 10 day period, a same 5 day period or a same 1 day period.

In another embodiment, the invention provides a pharmaceutical composition comprising EPA (e.g. E-EPA or ultra pure E-EPA) encapsulated in a capsule shell as described herein and having a baseline peroxide value not greater than about 10 meq/mg, about 9 meq/mg, about 8 meq/mg, about 7 meq/mg, about 6 meq/mg, about 5 meq/mg, about 4 meq/mg, about 3 meq/mg or about 2 meq/mg, wherein upon storage of the composition at 25° C. and 60% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition has a second peroxide value not greater than about 25 meq/mg, about 24 meq/mg, about 23 meq/mg, about 22 meq/mg, about 21 meq/mg, about 20 meq/mg, about 19 meq/mg, about 18 meq/mg, about 17 meq/mg, about 16 meq/mg, about 15 meq/mg, about 14 meq/mg, about 13 meq/mg, about 12 meq/mg, about 11 meq/mg, about 10 meq/mg, about 9 meq/mg, about 8 meq/mg, about 7 meq/mg, about 6 meq/mg, about 5 meq/mg, about 4 meq/mg, about 3 meq/mg or about 2 meq/mg.

In another embodiment, the invention provides a pharmaceutical composition comprising EPA (e.g. E-EPA or ultra pure E-EPA) encapsulated in a capsule shell as described herein and having a baseline peroxide value not greater than about 10 meq/mg, about 9 meq/mg, about 8 meq/mg, about 7 meq/mg, about 6 meq/mg, about 5 meq/mg, about 4 meq/mg, about 3 meq/mg or about 2 meq/mg, wherein upon storage of the composition at 30° C. and 65% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition has a second peroxide value not greater than about 25 meq/mg, about 24 meq/mg, about 23 meq/mg, about 22 meq/ mg, about 21 meq/mg, about 20 meq/mg, about 19 meq/mg, about 18 meq/mg, about 17 meq/mg, about 16 meq/mg, about 15 meq/mg, about 14 meq/mg, about 13 meq/mg, about 12 meq/mg, about 11 meq/mg, about 10 meq/mg, about 9 meq/mg, about 8 meq/mg, about 7 meq/mg, about 6 meq/mg, about 5 meq/mg, about 4 meq/mg, about 3 meq/mg or about 2 meq/mg.

In another embodiment, the invention provides a pharmaceutical composition comprising EPA (e.g. E-EPA or ultra pure E-EPA) encapsulated in a capsule shell as described herein and having a baseline peroxide value not greater than about 10 meq/mg, about 9 meq/mg, about 8 meq/mg, about 7 meq/mg, about 6 meq/mg, about 5 meq/mg, about 4 meq/mg, about 3 meq/mg or about 2 meq/mg, wherein upon storage of the composition at 40° C. and 75% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition has a second peroxide value not greater than about 25 meq/mg, about 24 meq/mg, about 23 meq/mg, about 22 meq/mg, about 21 meq/mg, about 20 meq/mg, about 19 meq/mg, about 18 meq/mg, about 17 meq/mg, about 16 meq/mg, about 15 meq/mg, about 14 meq/mg, about 13 meq/mg, about 12 meq/mg, about 11 meq/mg, about 10 meq/mg, about 9 meq/mg, about 8 meq/mg, about 7 meq/mg, about 6 meq/mg, about 5 meq/mg, about 4 meq/mg, about 3 meq/mg or about 2 meq/mg.

In another embodiment, the invention provides a pharmaceutical composition comprising EPA (e.g. E-EPA or ultra pure E-EPA) encapsulated in a capsule shell and having a baseline peroxide value not greater than about 10 meq/mg, about 9 meq/mg, about 8 meq/mg, about 7 meq/mg, about 6 meq/mg, about 5 meq/mg, about 4 meq/mg, about 3 meq/mg or about 2 meq/mg, wherein the capsule comprises a film-forming material and a plasticizer in a weight ratio of not less than 1.75:1 and wherein upon storage of the composition at 23° C. and 50% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition has a second peroxide value not greater than about 25 meq/mg, about 24 meq/mg, about 23 meq/mg, about 22 meq/mg, about 21 meq/mg, about 20 meq/mg, about 19 meq/mg, about 18 meq/mg, about 17 meq/mg, about 16 meq/mg, about 15 meq/mg, about 14 meq/mg, about 13 meq/mg, about 12 meq/mg, about 11 meq/mg g, about 10 meq/mg, about 9 meq/mg, about 8 meq/mg, about 7 meq/mg, about 6 meq/mg, about 5 meq/mg, about 4 meq/mg, about 3 meq/mg or about 2 meq/mg.

In another embodiment, the invention provides a pharmaceutical composition comprising EPA (e.g. E-EPA or ultra pure E-EPA) encapsulated in a capsule shell and having a baseline peroxide value not greater than about 10 meq/mg, about 9 meq/mg, about 8 meq/mg, about 7 meq/mg, about 6 meq/mg, about 5 meq/mg, about 4 meq/mg, about 3 meq/mg or about 2 meq/mg, wherein the capsule comprises a film-forming material and a plasticizer in a weight ratio of not less than 1.75:1 and wherein upon storage of the composition at 25° C. and 60% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition has a second peroxide value not greater than about 25 meq/mg, about 24 meq/mg, about 23 meq/mg, about 22 meq/mg, about 21 meq/mg, about 20 meq/mg, about 19 meq/mg, about 18 meq/mg, about 17 meq/mg, about 16 meq/mg, about 15 meq/mg, about 14 meq/mg, about 13 meq/mg, about 12 meq/mg, about 11 meq/mg, about 10 meq/mg, about 9 meq/mg, about 8 meq/mg, about 7 meq/mg, about 6 meq/mg, about 5 meq/mg, about 4 meq/mg, about 3 meq/mg or about 2 meq/mg.

In another embodiment, the invention provides a pharmaceutical composition comprising EPA (e.g. E-EPA or ultra pure E-EPA) encapsulated in a capsule shell and having a baseline peroxide value not greater than about 10 meq/mg, about 9 meq/mg, about 8 meq/mg, about 7 meq/mg, about 6 meq/mg, about 5 meq/mg, about 4 meq/mg, about 3 meq/mg or about 2 meq/mg, wherein the capsule comprises a film-forming material and a plasticizer in a weight ratio of not less than 1.75:1 and wherein upon storage of the composition at 30° C. and 65% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition has a second peroxide value not greater than about 25 meq/mg, about 24 meq/mg, about 23 meq/mg, about 22 meq/mg, about 21 meq/mg, about 20 meq/mg, about 19 meq/mg, about 18 meq/mg, about 17 meq/mg, about 16 meq/mg, about 15 meq/mg, about 14 meq/mg, about 13 meq/mg, about 12 meq/mg, about 11 meq/mg, about 10 meq/mg, about 9 meq/mg, about 8 meq/mg, about 7 meq/mg, about 6 meq/mg, about 5 meq/mg, about 4 meq/mg, about 3 meq/mg or about 2 meq/mg.

In another embodiment, the invention provides a pharmaceutical composition comprising EPA (e.g. E-EPA or ultra pure E-EPA) encapsulated in a capsule shell and having a baseline peroxide value not greater than about 10 meq/mg, about 9 meq/mg, about 8 meq/mg, about 7 meq/mg, about 6 meq/mg, about 5 meq/mg, about 4 meq/mg, about 3 meq/mg or about 2 meq/mg, wherein the capsule comprises a film-forming material and a plasticizer in a weight ratio of not less than 1.75:1 and wherein upon storage of the composition at 40° C. and 75% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition has a second peroxide value not greater than about 25 meq/mg, about 24 meq/mg, about 23 meq/mg, about 22 meq/mg, about 21 meq/mg, about 20 meq/mg, about 19 meq/mg, about 18 meq/mg, about 17 meq/mg, about 16 meq/mg, about 15 meq/mg, about 14 meq/mg, about 13 meq/mg, about 12 meq/mg, about 11 meq/mg, about 10 meq/mg, about 9 meq/mg, about 8 meq/mg, about 7 meq/mg, about 6 meq/mg, about 5 meq/mg, about 4 meq/mg, about 3 meq/mg or about 2 meq/mg.

In another embodiment, the invention provides a pharmaceutical composition comprising encapsulated EPA (e.g. E-EPA or ultra pure E-EPA) containing a labeled amount (i.e. initial amount) of EPA or E-EPA, wherein upon storage of the composition at 23° C. and 50% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition contains at least about 97%, about 98%, about 99%, about 99.5%, about 99.7%, about 99.9% or substantially all or 100% of the labeled amount of EPA or E-EPA, by weight.

In another embodiment, the invention provides a pharmaceutical composition comprising encapsulated EPA (e.g. E-EPA or ultra pure E-EPA) containing a labeled amount (i.e. initial amount) of EPA or E-EPA, wherein upon storage of the composition at 25° C. and 60% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition contains at least about 97%, about 98%, about 99%, about 99.5%, about 99.7%, about 99.9% or substantially all or 100% of the labeled amount of EPA or E-EPA, by weight.

In another embodiment, the invention provides a pharmaceutical composition comprising encapsulated EPA (e.g. E-EPA or ultra pure E-EPA) containing a labeled amount of EPA or E-EPA, wherein upon storage of the composition at 30° C. and 65% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition contains at least about 97%, about 98%, about 99%, about 99.5%, about 99.7%, about 99.9%, substantially all or 100% of the labeled amount of EPA or E-EPA, by weight.

In another embodiment, the invention provides a pharmaceutical composition comprising encapsulated EPA (e.g. E-EPA or ultra pure E-EPA) containing a labeled amount of EPA, wherein upon storage of the composition at 40° C. and 75% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition contains at least about 97%, about 98%, about 99%, about 99.5%, about 99.7%, about 99.8%, about 99.9%, substantially all or 100% of the labeled amount of EPA or E-EPA, by weight.

In another embodiment, the invention provides a pharmaceutical composition comprising encapsulated EPA containing a labeled amount of EPA or E-EPA, wherein upon storage of the composition at 23° C. and 50% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition contains not more than about 0.5%, not more than about 0.25%, not more than about 0.15%, not more than about 0.125%, not more than about 0.1%, not more than about 0.075%, not more than about 0.05% or substantially no degradation product and/or specified degradation product. The term "degradation product" in the present context means "an impurity resulting from a chemical change in the composition brought about during manufacture and/or storage of the composition by the effect of, for example, light, temperature, pH, water or by reaction with an excipient and/or the immediate container closure system." The "specified degradation product in the present context means "a degradation product, either identified or unidentified, that is individually listed and limited with a specific acceptance criterion in the product specification" for a particular product.

In another embodiment, the invention provides a pharmaceutical composition comprising encapsulated EPA (e.g. E-EPA or ultra pure E-EPA) containing a labeled amount of EPA or E-EPA, wherein upon storage of the composition at 25° C. and 60% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, the composition contains not more than about 0.5%, not more than about 0.25%, not more than about 0.15%, not more than about 0.125%, not more than about 0.1%, not more than about 0.075%, not more than about 0.05% or substantially no degradation product and/or specified degradation product.

In another embodiment, the invention provides a pharmaceutical composition comprising encapsulated EPA (e.g. E-EPA or ultra pure E-EPA) containing a labeled amount of EPA or E-EPA, wherein upon storage of the composition at 30° C. and 65% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, the composition contains not more than about 0.5% (by weight of the labeled EPA or E-EPA), not more than about 0.25%, not more than about 0.15%, not more than about 0.125%, not more than about 0.1%, not more than about 0.075%, not more than about 0.05% or substantially no degradation product and/or specified degradation product.

In another embodiment, the invention provides a pharmaceutical composition comprising encapsulated EPA (e.g. E-EPA or ultra pure E-EPA) containing a labeled amount of EPA or E-EPA, wherein upon storage of the composition at 40° C. and 75% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, the composition contains not more than about 0.5% (by weight of the labeled EPA or E-EPA), not more than about 0.25%, not more than about 0.15%, not more than about 0.125%, not more than about 0.1%, not more than about 0.075%, not more than about 0.05% or substantially no degradation product and/or specified degradation product.

In another embodiment, the invention provides a pharmaceutical composition comprising encapsulated EPA (e.g. E-EPA or ultra pure E-EPA) containing a labeled amount of EPA or E-EPA, wherein the capsule comprises a film-forming material, a hygroscopic plasticizer and a non-hygroscopic plasticizer and upon storage of the composition at 23° C. and 50% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, the composition contains not more than about 0.5% (by weight of the labeled EPA or E-EPA), not more than about 0.25%, not more than about 0.15%, not more than about 0.125%, not more than about 0.1%, not more than about 0.075%, not more than about 0.05% or substantially no degradation product and/or specified degradation product.

In another embodiment, the invention provides a pharmaceutical composition comprising encapsulated EPA (e.g. E-EPA or ultra pure E-EPA) containing a labeled amount of EPA, wherein the capsule comprises a film-forming material, a hygroscopic plasticizer and a non-hygroscopic plasticizer and upon storage of the composition at 25° C. and 60% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, the composition contains not more than about 0.5% (by weight of the labeled EPA or E-EPA), not more than about 0.25%, not more than about 0.15%, not more than about 0.125%, not more than about 0.1%, not more than about 0.075%, not more than about 0.05% or substantially no degradation product and/or specified degradation product.

In another embodiment, the invention provides a pharmaceutical composition comprising encapsulated EPA (e.g. E-EPA or ultra pure E-EPA) containing a labeled amount of EPA, wherein the capsule comprises a film-forming material, a hygroscopic plasticizer and a non-hygroscopic plasticizer and upon storage of the composition at 30° C. and 65% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, the composition contains not more than about 0.5% (by weight of the labeled EPA or E-EPA), not more than about 0.25%, not more than about 0.15%, not more than about 0.125%, not more than about 0.1%, not more than about 0.075%, not more than about 0.05% or substantially no degradation product and/or specified degradation product.

In another embodiment, the invention provides a pharmaceutical composition comprising EPA (e.g. E-EPA or ultra pure E-EPA) containing a labeled amount of EPA or E-EPA, wherein the capsule comprises a film-forming material, a hygroscopic plasticizer and a non-hygroscopic plasticizer and upon storage of the composition at 40° C. and 75% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, the composition contains not more than about 0.5% (by weight of the labeled EPA or E-EPA), not more than about 0.25%, not more than about 0.15%, not more than about 0.125%, not more than about 0.1%, not more than about 0.075%, not more than about 0.05% or substantially no degradation product and/or specified degradation product.

In another embodiment, the invention provides a pharmaceutical composition comprising encapsulated EPA (e.g. E-EPA or ultra pure E-EPA) containing a labeled amount of EPA or E-EPA, wherein the capsule comprises a film-forming material and a plasticizer in a weight ratio of about 2:5:1 to about 10:1 and upon storage of the composition at 23° C. and 50% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, the composition contains not more than about 0.5% (by weight of the labeled EPA or E-EPA), not more than about 0.25%, not more than about 0.15%, not more than about 0.125%, not more than about 0.1%, not more than about 0.075%, not more than about 0.05% or substantially no degradation product and/or specified degradation product.

In another embodiment, the invention provides a pharmaceutical composition comprising encapsulated EPA (e.g. E-EPA or ultra pure E-EPA) containing a labeled amount of EPA, wherein the capsule comprises a film-forming material and a plasticizer in a weight ratio of about 2:5:1 to about 10:1 and upon storage of the composition at 25° C. and 60% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition contains not more than about 0.5% (by weight of the labeled EPA or E-EPA), not more than about 0.25%, not more than about 0.15%, not more than about 0.125%, not more than about 0.1%, not more than about 0.075%, not more than about 0.05% or substantially no degradation product and/or specified degradation product.

In another embodiment, the invention provides a pharmaceutical composition comprising encapsulated (e.g. E-EPA or ultra pure E-EPA) containing a labeled amount of EPA or E-EPA, wherein the capsule comprises a film-forming material and a plasticizer in a weight ratio of about 2:5:1 to about 10:1 and upon storage of the composition at 30° C. and 65% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition contains not more than about 0.5% (by weight of the labeled EPA or E-EPA), not more than about 0.25%, not more than about 0.15%, not more than about 0.125%, not more than about 0.1%, not more than about 0.075%, not more than about 0.05% or substantially no degradation product and/or specified degradation product.

In another embodiment, the invention provides a pharmaceutical composition comprising encapsulated (e.g. E-EPA or ultra pure E-EPA) containing a labeled amount of EPA or E-EPA, wherein the capsule comprises a film-forming material and a plasticizer in a weight ratio of about 2:5:1 to about 10:1 and upon storage of the composition at 40° C. and 75% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, said composition contains not more than about 0.5% (by weight of the labeled EPA or E-EPA), not more than about 0.25%, not more than about 0.15%, not more than about 0.125%, not more than about 0.1%, not more than about 0.075%, not more than about 0.05% or substantially no degradation product and/or specified degradation product.

In another embodiment, the present invention provides a pharmaceutical composition comprising about 0.5 g to about 1.5 g of EPA (e.g. E-EPA or ultra pure E-EPA) having a labeled amount of EPA or E-EPA encapsulated in a pharmaceutical capsule, wherein upon storage at 15° C. to 30° C. for a period of about 6 months, 12 months, 18 months, 24 months, 30 months, or 36 months, at least about 97%, about 98%, about 99%, about 99.5%, about 99.6%, about 99.7%, about 99.8%, about 99.9% or substantially all of the labeled amount of EPA is still present in the composition. In a related embodiment, the composition has not reached its labeled expiration date during said storage period.

In various embodiments, capsule shells suitable for use in the present invention comprise one or more film-forming materials, one or more plasticizers and optionally a solvent (e.g. water). In a related embodiment, the film-forming material comprises gelatin. In another embodiment, the plasticizer comprises a hygroscopic and/or non-hygroscopic plasticizer. In still another embodiment, the capsule shell comprises a film-forming material, a hygroscopic plasticizer, a non-hygroscopic plasticizer and a solvent.

In another embodiment, the capsule shell comprises about 30% to about 70% or about 40% to about 65%, by weight, of a film-forming material, about 15% to about 40% or about 20% to about 35%, by weight, of one or more plasticizers, and about 3% to about 15% or about 5% to about 10%, by weight, solvent such as water. Optionally, the capsules may also contain additives such as colorants, flavorants, preservatives, disintegrants, surfactants, fragrances, sweeteners, etc.

Capsules suitable for use in various embodiments of the invention comprise a film-forming material, for example gelatin. Gelatin is typically manufactured from animal byproducts that contain collagen, for example in the bones, skin, and connective tissue. Methods of producing gelatin from animal byproducts are well-known in the art. In various embodiments, the gelatin may be alkali-treated gelatin, acid-treated gelatin, chemically modified gelatin, or mixtures thereof. Methods to produce alkali-treated gelatin, acid-treated gelatin, and chemically modified gelatin are known in the art and are described, for example in Nakamura et al., U.S. 2003/0195246, hereby incorporated by reference herein in its entirety.

The film-forming material may also comprise, for example, non-animal based hydrocolloids such as carrageenan, alkylated or hydroxyalkylated cellulose ethers, starch, alpha-starch, hydroxyalkyl starch, sodium alginate, sodium salt of a gelatin copolymer and acrylic acid.

In another embodiment, the film-forming material can comprise a 20:80 to about 80:20, by weight, mixture, for example a 60:40, by weight mixture of hydroxypropyl methyl cellulose and polyvinyl alcohol (e.g. about 70% to about 90%, for example about 88.0% saponified; and about 30 to about 50, for example about 45.0 centipoise viscosity). In another embodiment, the film-forming material can comprise a 20:80 to about 80:20, by weight, mixture, for example a 60:40, by weight, mixture of hydroxyethyl cellulose and polyvinyl alcohol (e.g. about 70% to about 99.9%, for example about 98.5% saponified; and about 2 to about 30, for example about 5.5 centipoise viscosity).

A suitable capsule shell may further comprise an elasticity reducing gel extender as part of the film-forming material. An elasticity reducing gel extender can comprise starch, starch derivatives such as high amylose starch, oxidized starch, esterified starch, acid-thinned starch, etherified starch, hydrolyzed starch, hydrolyzed and hydrogenated starch, enzyme treated starch, and modified celluloses or other natural or modified natural biopolymers such as bacterial polysaccharides, vegetable gums, or other exudates including alginates, carrageenans, guar gum, gum arabic, gum ghatti, gum karaya, gum tragacanth, pectins, tamarind gum, xanthan gum, and dextrans as well as synthetic polymers such as carbon chain polymers of the vinyl and acrylic types as well as heterochains of the polyoxide and polyamine types including polyethylene oxide, polypropylene oxide, polyoxymethylene, polytrimethylene oxide, block copolymers of ethylene oxide, block copolymers of polyethylene oxide, polyvinyl methyl ether, polyethylene imine, polyacrylic acid, polyacrylamide, polymethacrylic acid, polymethacrylamide, poly(N,N-Dimethylacrylamide), poly(N-Isopropylacrylamide), poly(N-Acrylylglycinamide), poly(N-Methyacrylyglycinamide), acrylic copolymers, polyvinyl alcohol polyvinylacetate, polyvinyl acetate-co-vinyl alcohol, polyvinylpyrrolidone, N-Methylpyrrolidone, N-Ethylpyrrolidone, N-Vinylpyrrolidone, sarcosine anhydride, polyvinyloxazolindone, and polyvinylmethyloxazolidone. The starch or other elasticity reducing gel extender may be added into the formulation in amounts ranging from about 8% to about 30% by weight, for example about 10% to about 16%, by weight.

Capsule shells suitable for use in various embodiments of the invention can comprise one or more plasticizers, for example hygroscopic and/or non-hygroscopic plasticizers. Non-limiting examples of suitable hygroscopic plasticizers include glycerin, sorbitol and alkylene glycols (e.g., propylene glycol and low molecular weight polyethylene glycols). Non-limiting examples of suitable non-hygroscopic plasticizers include partially dehydrated hydrogenated glucose syrup, maltitol, maltose, lactitol, xylitol, erythritol and polyethylene glycols of average molecular weights from about 400 to about 6000.

In one embodiment, a capsule shell suitable for use in a composition of the invention has a hygroscopic plasticizer to non-hygroscopic plasticizer weight ratio of about 1:1 to about 8:1, about 2:1 to about 6:1, about 3:1 to about 5:1, for example about 4:1, about 4.25:1, about 4.5:1 or about 4.75:1.

In another embodiment, a capsule shell suitable for use in a composition of the invention has a gelatin to glycerol weight ratio of about 2:5:1 to about 10:1, about 3.5:1 to about 9:1, about 4:1 to about 8:1, or about 5:1 to about 7:1, for example at least about 2.6:1, at least about 2.7:1, at least about 2.8:1, at least about 2.9:1, at least about 3:1, at least about 3.1:1, at least about 3.2:1, at least about 3.3:1, at least about 3.4:1, at least about 3.5:1, at least about 3.6:1, at least about 3.7:1, at least about 3.8:1, at least about 3.9:1, at least about 4.0:1, at least about 4.1:1, at least about 4.2:1, at least about 4.3:1, at least about 4.4:1, at least about 4.5:1, at least about 4.6:1, at least about 4.7:1, at least about 4.8:1, at least about 4.9:1, at least about 5.0:1, at least about 5.1:1, or at least about 5.2:1.

In another embodiment, a suitable capsule shell has a film-forming material (e.g. gelatin) to total plasticizer weight ratio of about 1.75 to about 5, about 1.78 to about 3, or about 1.8 to about 2.5, for example at least about 1.76, at least about 1.77, at least about 1.78, at least about 1.79, at least about 1.8, at least about 1.81, at least about 1.82, at least about 1.83, or at least about 1.84.

In another embodiment, the capsule shell has: (1) a gelatin to glycerol weight ratio of about 2:5:1 to about 10:1, about 3.5:1 to about 9:1, about 4:1 to about 8:1, or about 5:1 to about 7:1, for example at least about 2.6:1, at least about 2.7:1, at least about 2.8:1, at least about 2.9:1, at least about 3:1, at least about 3.1:1, at least about 3.2:1, at least about 3.3:1, at least about 3.4:1, at least about 3.5:1, at least about 3.6:1, at least about 3.7:1, at least about 3.8:1, at least about 3.9:1, at least about 4.0:1, at least about 4.1:1, at least about 4.2:1, at least about 4.3:1, at least about 4.4:1, at least about 4.5:1, at least about 4.6:1, at least about 4.7:1, at least about 4.8:1, at least about 4.9:1, at least about 5.0:1, at least about 5.1:1, or at least about 5.2:1; and/or (2) a gelatin to total plasticizer weight ratio of about 1.75:1 to about 5:1, about 1.78:1 to about 3:1, or about 1.8:1 to about 2.5:1, for example at least about 1.76:1, at least about 1.77:1, at least about 1.78:1, at least about 1.79:1, at least about 1.8:1, at least about 1.81, at least about 1.82, at least about 1.83, or at least about 1.84.

In one embodiment, the capsule shell comprises one or more of: gelatin in an amount of about 50% to about 70%; glycerol in an amount of about 5% to about 15%; sorbitol in an amount of about 15% to about 25%; and/or maltitol in an amount of about 3% to about 10%, by weight of the non-aqueous components. Such a capsule can further comprise about 2% to about 16% by weight of a solvent such as water.

In another embodiment, a capsule shell suitable for use in compositions of the present invention can be prepared using a gel mass comprising about 40% to about 50% gelatin, about 2% to about 12% glycerol, about 10% to about 20% sorbitol solution, about 2% to about 10% maltitol syrup, and about 20% to about 35% water, by weight. In one embodiment, a capsule shell suitable for us in a composition of the present invention can be prepared using a gel mass comprising about 45% gelatin by weight, about 7% glycerol by weight, about 17% sorbitol solution (e.g. 30% water) by weight, about 6% maltitol syrup (e.g. 15%-32% water) by weight, and about 25% water by weight. Capsules prepared from such a gel mass can be dried to about 2% to about 12% final moisture content. Capsules prepared by such a process that contain EPA (e.g. E-EPA or ultra pure E-EPA), and methods of using the same in the treatment of cardiovascular-related diseases represent further embodiments of the invention. Capsule compositions as described herein can further comprise coatings, for example enteric polymer or wax coatings.

In one embodiment, a composition of the invention provides a relatively rapid dissolution profile yet still maintains excellent stability of the encapsulated material (e.g. EPA). In a related embodiment, a composition of the invention has a dissolution profile (as measured by Rotating Dialysis Cell Dissolution (RDC) Apparatus under the conditions set forth herein below) of one or more of the following: (1) at least about 20%, at least about 23% or at least about 25% of E-EPA is dissolved by 10 minutes; (2) at least about 45%, at least about 50% or at least about 55% of E-EPA is dissolved by 30 minutes; (3) at least about 80%, at least about 82%, at least about 85% or at least about 87% of E-EPA is dissolved by 60 minutes; and/or (4) at least about 95%, at least about 97% or 100% of E-EPA is dissolved by 100 minutes. In a related embodiment, the fill material still retains the stability/peroxide values as set forth throughout this specification.

In another embodiment, a composition of the invention provides a relatively short $T_{max}$ yet still maintains excellent stability of the encapsulated material (e.g. EPA). In a related embodiment, a composition of the invention, upon administration to a subject, exhibits an EPA $T_{max}$ less than 6 hours, less than 5.8 hours, less than 5.6 hours, less than 5.4 hours or less than 5.2 hours, for example about 4.8 to about 5.2 hours. In a related embodiment, the fill material still retains the stability/peroxide values as set forth throughout this specification.

In one embodiment, a method for treatment and/or prevention of a cardiovascular-related disease using a composition as described herein is provided. The term "cardiovascular-related disease" herein refers to any disease or disorder of the heart or blood vessels (i.e. arteries and veins) or any symptom thereof. The term "cardiovascular-related disease" herein refers to any disease or disorder of the heart or blood vessels (i.e. arteries and veins) or any symptom thereof, or any disease or condition that causes or contributes to a cardiovascular disease." Non-limiting examples of cardiovascular-related diseases include acute cardiac ischemic events, acute myocardial infarction, angina, angina pectoris, arrhythmia, atrial fibrulation, atherosclerosis, arterial fibrillation, cardiac insufficiency, cardiovascular disease, chronic heart failure, chronic stable angina, congestive heart failure, coronary artery disease, coronary heart disease, deep vein thrombosis, diabetes, diabetes mellitus, diabetic neuropathy, diastolic dysfunction in subjects with diabetes mellitus, edema, essential hypertension, eventual pulmonary embolism, fatty liver disease, heart disease, heart failure, homozygous familial hypercholesterolemia (HoFH), homozygous familial sitosterolemia, hypercholesterolemia, hyperlipidemia, hyperlipidemia in HIV positive subjects, hypertension, hypertriglyceridemia, ischemic complications in unstable angina and myocardial infarction, low blood pressure, metabolic syndrome, mixed dyslipidemia, moderate to mild heart failure, myocardial infarction, obesity management, paroxysmal atrial/arterial fibrillation/fibrulation/flutter, paroxysmal supraventricular tachycardias (PSVT), particularly severe or rapid onset edema, platelet aggregation, primary hypercholesterolemia, primary hyperlipidemia, pulmonary arterial hypertension, pulmonary hypertension, recurrent hemodynamically unstable ventricular tachycardia (VT), recurrent ventricular arrhythmias, recurrent ventricular fibrillation (VF), ruptured aneurysm, sitisterolemia, stroke, supraventricular tachycardia, symptomatic atrial fibrillation/flutter, tachycardia, type-II diabetes, vascular disease, venous thromboembolism, ventricular arrhythmias, and other cardiovascular events.

The term "treatment" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In one embodiment, the present invention provides a method of blood lipid therapy comprising administering to a subject or subject group in need thereof a pharmaceutical composition as described herein. In another embodiment, the subject or subject group has hypertriglyceridemia, hypercholesterolemia, mixed dyslipidemia and/or very high triglycerides.

In another embodiment, the subject or subject group being treated has a baseline triglyceride level (or median baseline triglyceride level in the case of a subject group), fed or fasting, of at least about 300 mg/dl, at least about 400 mg/dl, at least about 500 mg/dl, at least about 600 mg/dl, at least about 700 mg/dl, at least about 800 mg/dl, at least about 900 mg/dl, at least about 1000 mg/dl, at least about 1100 mg/dl, at least about 1200 mg/dl, at least about 1300 mg/dl, at least about 1400 mg/dl, or at least about 1500 mg/dl, for example about 400 mg/dl to about 2500 mg/dl, about 450 mg/dl to about 2000 mg/dl or about 500 mg/dl to about 1500 mg/dl.

In another embodiment, the subject or subject group being treated in accordance with methods of the invention has previously been treated with Lovaza® and has experienced an increase in, or no decrease in, LDL-C levels and/or non-HDL-C levels. In one such embodiment, Lovaza® therapy is discontinued and replaced by a method of the present invention.

In another embodiment, the subject or subject group being treated in accordance with methods of the invention exhibits a fasting baseline absolute plasma level of free EPA (or mean thereof in the case of a subject group) not greater than about 0.70 nmol/ml, not greater than about 0.65 nmol/ml, not greater than about 0.60 nmol/ml, not greater than about 0.55 nmol/ml, not greater than about 0.50 nmol/ml, not greater than about 0.45 nmol/ml, or not greater than about 0.40 nmol/ml. In another embodiment, the subject or subject group being treated in accordance with methods of the invention exhibits a baseline fasting plasma level (or mean thereof) of free EPA, expressed as a percentage of total free fatty acid, of not more than about 3%, not more than about 2.5%, not more than about 2%, not more than about 1.5%, not more than about 1%, not more than about 0.75%, not more than about 0.5%, not more than about 0.25%, not more than about 0.2% or not more than about 0.15%. In one such embodiment, free plasma EPA and/or total fatty acid levels are determined prior to initiating therapy.

In another embodiment, the subject or subject group being treated in accordance with methods of the invention exhibits a fasting baseline absolute plasma level of total fatty acid (or mean thereof) not greater than about 250 nmol/ml, not greater than about 200 nmol/ml, not greater than about 150 nmol/ml, not greater than about 100 nmol/ml, or not greater than about 50 nmol/ml.

In another embodiment, the subject or subject group being treated in accordance with methods of the invention exhibits a fasting baseline plasma, serum or red blood cell membrane EPA level not greater than about 70 µg/ml, not greater than about 60 µg/ml, not greater than about 50 µg/ml, not greater than about 40 µg/ml, not greater than about 30 µg/ml, or not greater than about 25 µg/ml.

In another embodiment, methods of the present invention comprise a step of measuring the subject's (or subject group's mean) baseline lipid profile prior to initiating therapy. In another embodiment, methods of the invention comprise the step of identifying a subject or subject group having one or more of the following: baseline non-HDL-C value of about 200 mg/dl to about 400 mg/dl, for example at least about 210 mg/dl, at least about 220 mg/dl, at least about 230 mg/dl, at least about 240 mg/dl, at least about 250 mg/dl, at least about 260 mg/dl, at least about 270 mg/dl, at least about 280 mg/dl, at least about 290 mg/dl, or at least about 300 mg/dl; baseline total cholesterol value of about 250 mg/dl to about 400 mg/dl, for example at least about 260 mg/dl, at least about 270 mg/dl, at least about 280 mg/dl or at least about 290 mg/dl; baseline vLDL-C value of about 140 mg/dl to about 200 mg/dl, for example at least about 150 mg/dl, at least about 160 mg/dl, at least about 170 mg/dl, at least about 180 mg/dl or at least about 190 mg/dl; baseline HDL-C value of about 10 to about 60 mg/dl, for example not more than about 40 mg/dl, not more than about 35 mg/dl, not more than about 30 mg/dl, not more than about 25 mg/dl, not more than about 20 mg/dl, or not more than about 15 mg/dl; and/or baseline LDL-C value of about 50 to about 300 mg/dl, for example not less than about 100 mg/dl, not less than about 90 mg/dl, not less than about 80 mg/dl, not less than about 70 mg/dl, not less than about 60 mg/dl or not less than about 50 mg/dl.

In one embodiment, compositions of the invention are packaged in blister packs. In another embodiment, the blister packs comprise PCTFE (for example 50μ) laminated with water based adhesive to clear PVC (for example 1900μ) which are heat sealed to aluminum foil).

In a related embodiment, upon treatment in accordance with the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits one or more of the following outcomes:

(a) reduced triglyceride levels compared to baseline or a placebo arm;
(b) reduced Apo B levels compared to baseline or a placebo arm;
(c) increased HDL-C levels compared to baseline or a placebo atm;
(d) no increase in LDL-C levels compared to baseline or a placebo arm;
(e) a reduction in LDL-C levels compared to baseline or a placebo arm;
(f) a reduction in non-HDL-C levels compared to baseline or a placebo arm;
(g) a reduction in vLDL levels compared to baseline or a placebo aim;
(h) an increase in apo A-I levels compared to baseline or a placebo arm;
(i) an increase in apo A-I/apo B ratio compared to baseline or a placebo arm;
(j) a reduction in lipoprotein A levels compared to baseline or a placebo arm;
(k) a reduction in LDL particle number compared to baseline or a placebo arm;
(l) an increase in mean LDL size compared to baseline or a placebo arm;
(m) a reduction in remnant-like particle cholesterol compared to baseline or a placebo arm;
(n) a reduction in oxidized LDL compared to baseline or a placebo arm;
(o) no change or a reduction in fasting plasma glucose (FPG) compared to baseline or a placebo arm;
(p) a reduction in hemoglobin $A_{1c}$ ($HbA_{1c}$) compared to baseline or a placebo arm;
(q) a reduction in homeostasis model insulin resistance compared to baseline or a placebo arm;
(r) a reduction in lipoprotein associated phospholipase A2 compared to baseline or a placebo arm;
(s) a reduction in intracellular adhesion molecule-1 compared to baseline or a placebo arm;
(t) a reduction in interleukin-6 compared to baseline or a placebo at it;
(u) a reduction in plasminogen activator inhibitor-1 compared to baseline or a placebo arm;
(v) a reduction in high sensitivity C-reactive protein (hsCRP) compared to baseline or a placebo arm;
(w) an increase in serum phospholipid EPA compared to baseline or a placebo arm;
(x) an increase in red blood cell membrane EPA compared to baseline or a placebo arm; and/or
(y) a reduction or increase in one or more of serum phospholipid and/or red blood cell content of docosahexaenoic acid (DHA), docosapentaenoic acid (DPA), arachidonic acid (AA), palmitic acid (PA), staeridonic acid (SA) or oleic acid (OA) compared to baseline or a placebo arm.

In one embodiment, methods of the present invention comprise measuring baseline levels of one or more markers set forth in (a)-(y) above prior to dosing the subject or subject group. In another embodiment, the methods comprise administering a composition as disclosed herein to the subject after baseline levels of one or more markers set forth in (a)-(y) are determined, and subsequently taking an additional measurement of said one or more markers.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more, any 24 or more, or all 25 of outcomes (a)-(y) described immediately above.

In another embodiment, upon treatment with a composition of the present invention, the subject or subject group exhibits one or more of the following outcomes:

(a) a reduction in triglyceride level of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or a placebo arm;

(b) a less than 30% increase, less than 20% increase, less than 10% increase, less than 5% increase or no increase in non-HDL-C levels or a reduction in non-HDL-C levels of at least about 1%, at least about 3%, at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or a placebo arm;

(c) substantially no change, no change or an increase in HDL-C levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or a placebo arm;

(d) a less than 60% increase, less than 50% increase, less than 40% increase, less than 30% increase, less than 20% increase, less than 10% increase, less than 5% increase or no increase in LDL-C levels or a reduction in LDL-C levels of at least about 5%, at least about 10%, at least about 15%, at least about 20%, at least about 25%, at least about 30%, at least about 35%, at least about 40%, at least about 45%, at least about 50%, at least about 55%, at least about 55% or at least about 75% (actual % change or median % change) as compared to baseline or a placebo arm;

(e) a decrease in Apo B levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or a placebo arm;

(f) a reduction in vLDL levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(g) an increase in apo A-I levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(h) an increase in apo A-I/apo B ratio of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(i) a reduction in lipoprotein(a) levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(j) a reduction in mean LDL particle number of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(k) an increase in mean LDL particle size of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(l) a reduction in remnant-like particle cholesterol of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(m) a reduction in oxidized LDL of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(n) substantially no change, no change or a reduction in fasting plasma glucose (FPG) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(o) substantially no change, no change or a reduction in hemoglobin $A_{1c}$ (HbA$_{1c}$) of at least about 5%, at least about 10%, at least about 15%, at least about 20%, at least about 25%, at least about 30%, at least about 35%, at least about 40%, at least about 45%, or at least about 50% (actual % change or median % change) compared to baseline or a placebo arm;

(p) a reduction in homeostasis model index insulin resistance of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(q) a reduction in lipoprotein associated phospholipase A2 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(r) a reduction in intracellular adhesion molecule-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(s) a reduction in interleukin-6 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(t) a reduction in plasminogen activator inhibitor-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(u) a reduction in high sensitivity C-reactive protein (hsCRP) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

(v) an increase in serum, plasma and/or RBC EPA of at least about 5%, at least about 10%, at least about 15%, at least about 20%, at least about 25%, at least about 30%, at least about 35%, at least about 40%, at least about 45%, at least about 50%, at least about 100%, at least about 200% or at least about 400% (actual % change or median % change) compared to baseline or a placebo arm;

(w) an increase in serum phospholipid and/or red blood cell membrane EPA of at least about 5%, at least about 10%, at least about 15%, at least about 20%, at least about 25%, at least about 30%, at least about 35%, at least about 40%, at least about 45%, r at least about 50%, at least about 100%, at least about 200%, or at least about 400% (actual % change or median % change) compared to baseline or a placebo arm;

(x) a reduction or increase in one or more of serum phospholipid and/or red blood cell DHA, DPA, AA, PA and/or OA of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline or a placebo arm; and/or (y) a reduction in total cholesterol of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline or a placebo arm.

In one embodiment, methods of the present invention comprise measuring baseline levels of one or more markers set forth in (a)-(y) prior to dosing the subject or subject group. In another embodiment, the methods comprise administering a composition as disclosed herein to the subject after baseline levels of one or more markers set forth in (a)-(y) are determined, and subsequently taking a second measurement of the one or more markers as measured at baseline for comparison thereto.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of any 20 or more of, any 21 or more of, any 22 or more of, any 23 or more of, any 24 or more of, or all 25 of outcomes (a)-(y) described immediately above.

Parameters (a)-(y) can be measured in accordance with any clinically acceptable methodology. For example, triglycerides, total cholesterol, HDL-C and fasting blood sugar can be sample from serum and analyzed using standard photometry techniques. VLDL-TG, LDL-C and VLDL-C can be calculated or determined using serum lipoprotein fractionation by preparative ultracentrifugation and subsequent quantitative analysis by refractometry or by analytic ultracentrifugal methodology. Apo A1, Apo B and hsCRP can be determined from serum using standard nephelometry techniques. Lipoprotein (a) can be determined from serum using standard turbidimetric immunoassay techniques. LDL particle number and particle size can be determined using nuclear magnetic resonance (NMR) spectrometry. Remnants lipoproteins and LDL-phospholipase A2 can be determined from EDTA plasma or serum and serum, respectively, using enzymatic immunoseparation techniques. Oxidized LDL, intercellular adhesion molecule-1 and interleukin-2 levels can be determined from serum using standard enzyme immunoassay techniques. These techniques are described in detail in standard textbooks, for example Tietz Fundamentals of Clinical Chemistry, $6^{th}$ Ed. (Burtis, Ashwood and Borter Eds.), WB Saunders Company.

In one embodiment, subjects fast for up to 12 hours prior to blood sample collection, for example about 10 hours.

In another embodiment, the present invention provides a method of treating or preventing primary hypercholesterolemia and/or mixed dyslipidemia (Fredrickson Types IIa and IIb) in a patient in need thereof, comprising administering to the patient one or more compositions as disclosed herein. In a related embodiment, the present invention provides a method of reducing triglyceride levels in a subject or subjects when treatment with a statin or niacin extended-release monotherapy is considered inadequate (Frederickson type IV hyperlipidemia).

In another embodiment, the present invention provides a method of treating or preventing risk of recurrent nonfatal myocardial infarction in a patient with a history of myocardial infarction, comprising administering to the patient one or more compositions as disclosed herein.

In another embodiment, the present invention provides a method of slowing progression of or promoting regression of atherosclerotic disease in a patient in need thereof, comprising administering to a subject in need thereof one or more compositions as disclosed herein.

In another embodiment, the present invention provides a method of treating or preventing very high serum triglyceride levels (e.g. Types IV and V hyperlipidemia) in a patient in need thereof, comprising administering to the patient one or more compositions as disclosed herein.

In another embodiment, the present invention provides a method of treating subjects having very high serum triglyceride levels (e.g. greater than 1000 mg/dl or greater than 2000 mg/dl) and that are at risk of developing pancreatitis, comprising administering to the patient one or more compositions as disclosed herein.

In one embodiment, a composition of the invention is administered to a subject in an amount sufficient to provide a daily dose of eicosapentaenoic acid of about 1 mg to about 10,000 mg, 25 about 5000 mg, about 50 to about 3000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg or about 2500 mg.

In another embodiment, any of the methods disclosed herein are used in treatment or prevention of a subject or subjects that consume a traditional Western diet. In one embodiment, the methods of the invention include a step of identifying a subject as a Western diet consumer or prudent diet consumer and then treating the subject if the subject is deemed a Western diet consumer. The term "Western diet"

herein refers generally to a typical diet consisting of, by percentage of total calories, about 45% to about 50% carbohydrate, about 35% to about 40% fat, and about 10% to about 15% protein. A Western diet may alternately or additionally be characterized by relatively high intakes of red and processed meats, sweets, refined grains, and desserts, for example more than 50%, more than 60% or more or 70% of total calories come from these sources.

EXAMPLES

The following examples are for illustrative purposes only and should not be construed as limiting the invention in any manner.

Example 1

A Test Composition (TC) was prepared comprising ultra-pure Ethyl-EPA (>96% E-EPA, ~3% related fatty acid substances (no DHA), and ~0.2% alpha tocopherol) filled into soft gelatin capsule shells (~500 mg fill weight per capsule) prepared from a gel comprising gelatin (~44%), glycerol (~7%), sorbitol solution (~17%), maltitol solution, gelatin and purified water. A Comparative Composition (CC) was made comprising the same fill as the Test Composition but filled into Type IIa Capsules made from a gel comprising of glycerol (~20%), gelatin (43.4%) and water (~36.6%).

Test Compositions and Comparative Compositions were then placed in polybags which were sealed and stored at either 25° C./60% RH or 30° C./65% RH for a period of 1, 3, or 6 months. At the end of storage, capsules were opened and peroxide value of the fill material was analyzed. Results are shown in Table 1 (average of capsules from three different batches).

TABLE 1

Peroxide Values (meq/mg) Upon Storage.

| Composition | Baseline | 1 Month | 3 Month | 6 Month |
|---|---|---|---|---|
| Storage at 25° C./60% RH | | | | |
| TC | 1.6 | — | 3.2 | 3.4 |
| CC | 1.9 | — | 3.4 | 9.6 |
| Storage at 30° C./65% RH | | | | |
| TC | 1.6 | 2.0 | 3.6 | 4.8 |
| CC | 1.8 | 1.9 | 3.5 | 12.5 |

As is seen in Table 1, the Test Composition fill material exhibited much lower peroxide values after 6 months of storage under both sets of storage conditions. No significant differences were observed between the Test Composition and Comparative Composition fill material in terms of potency of EPA-E and related substances throughout the duration of the study.

Example 2

Test Compositions and Comparative Compositions of Example 1 were prepared and packaged in blister packaging (50μ PCTFE laminated with water based adhesive to 190μ clear PVC and heat sealed to aluminum foil). Packaged Test Compositions and Comparative Compositions were then stored at either 25° C./60% RH or 40° C./70% RH for a period of 1, 3, 6, 12 or 36 months. At the end of storage, capsules were opened and the peroxide values of the fill contents analyzed as shown in Table 2 (average of the three batches).

TABLE 2

Peroxide Values (meq/mg) Upon Storage.

| | Baseline | 1 Mo. | 3 Mo. | 6 Mo. | 9 Mo. | 12 Mo. |
|---|---|---|---|---|---|---|
| Storage at 25° C./60% RH | | | | | | |
| TC | 2.5 | — | 1.1 | 2.1 | 2.2 | 5.4 |
| CC | 2.6 | — | 5.1 | 8.3 | 9.7 | 11.1 |
| Storage at 40° C./75% RH | | | | | | |
| TC | 2.5 | 2.1 | 3.2 | 4.9 | — | — |
| CC | 2.6 | 3.4 | 10.6 | 18.8 | — | — |

As is seen in Table 2, the Test Composition exhibited much lower peroxide values after 3, 6, 9 and 12 months of storage at 25° C./60% RH and after 1, 3 and 6 months of storage at 40° C./75% RH as compared to the Comparative Compositions.

At 40° C., the Test Composition showed an average decrease in E-EPA potency of 0.30% per month whereas the Comparative Compositions showed an average decrease in E-EPA potency of 0.44% per month. However, similar results were not obtained with the same batches in Example 1 (not stored in blister packages). Additionally, the related substances measurements did not show any concomitant increase suggesting normal analytic variation may be responsible.

When the peroxide values were forced to linear trendlines, average slope values between the Test Compositions in Experiment 1 (no blister packaging) and Experiment 2 (blister packaging) were similar indicating that the packaging is likely not responsible for prevention of oxidation.

TABLE 3

Peroxide Value: Linear Slope Comparison Between Example 1 and Example 2

| Storage | Test Composition Slope (meq/kg/mo.) | | Comparative Composition Slope (meq/kg/mo.) | |
|---|---|---|---|---|
| Conditions | Example 1 | Example 2 | Example 1 | Example 2 |
| 25° C./60% RH | 0.33 | 0.35 | 1.45 | 1.03 |
| 40° C./75% RH | 0.56 | 0.66 | 1.81 | 3.00 |

Example 3

A dissolution test was performed on capsules of Example 1 containing 500 mg E-EPA using the Rotating Dialysis Cell method set forth in Yamazaki et al., *Dissolution tests by RDC method for soft gelatin capsules containing ethyl icosapentate*, Pharmaceutical Technology Japan, 15: 595-603 (1999). Conditions were as set forth below:

| | |
|---|---|
| RDC Cell: | PharmaTest |
| Paddle speed: | 100 rpm |
| Temperature: | 37° C. |
| Filter: | Millipore hydrophobic filter sheets |
| Inner media: | JP pH 1.2 disintegration media |
| Outer Media: | Absolute Ethanol |
| Samples: | 5 ml taken at 10, 20, 30, 40, 60, 100 and 120 minutes |

The samples were analyzed against a reference standard prepared in ethanol at 0.5 mg/ml, the amount of product dissolved at each time point was then calculated. A good dissolution profile was obtained with a $Q_{85}$ of approximately 60 minutes and a profile very similar to that generated by Yamazaki (JP data; succinated gelatin capsules). Dissolution profile of the inventive capsule composition was also evaluated by the paddle method in media containing buffer, SDS and IPA (100 rpm paddle speed, 1000 ml, 37° C.). Samples were removed at intervals and analyzed against a standard solution (9.5 ml/ml in methanol) by HPCL. All data are shown in FIG. 1.

Example 4

Figure 2:
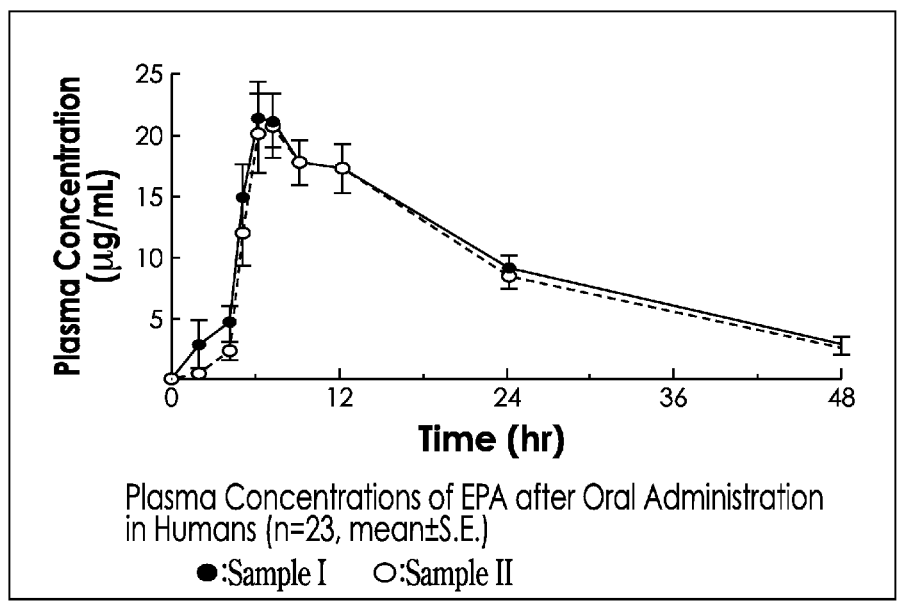
FIG. 2 shows bioavailability of 300 mg of EPA in succinated gelatin capsules.
Figure 3:
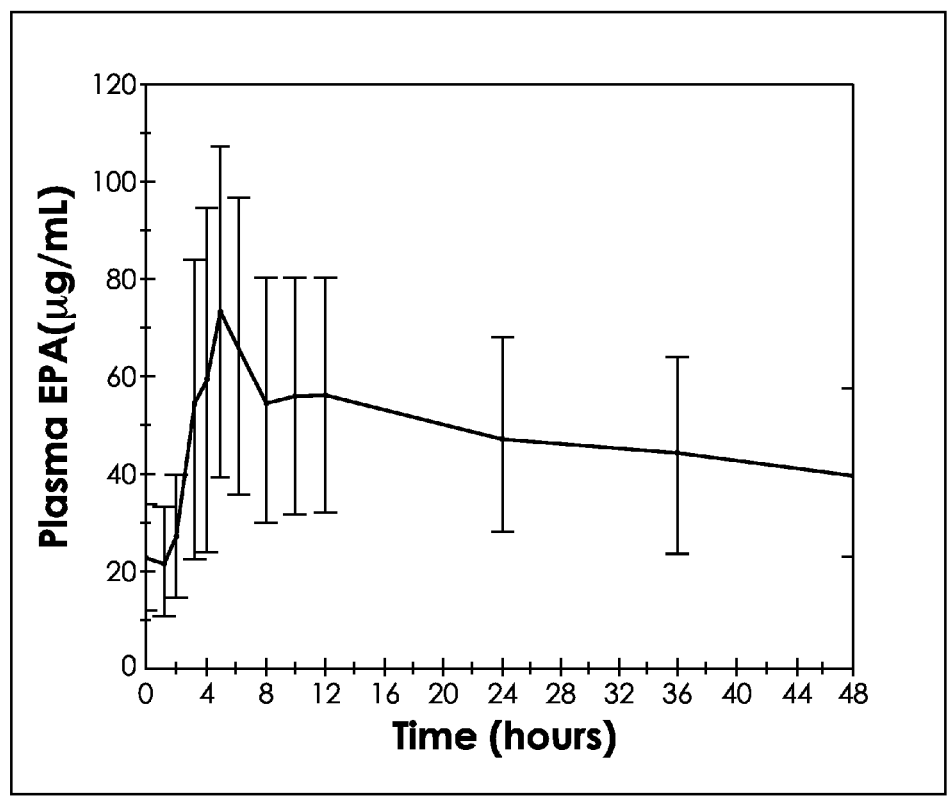
FIG. 3 shows bioavailability of an inventive AMR101 capsule composition containing ~500 mg E-EPA.

Bioavailability data were obtained for a capsule shell according to Example 1 containing 500 mg E-EPA (AMR101) and were compared against reported by Yamazaki data for 300 mg Epadel capsules (succinated gelatin; Comparitor 1 and Comparitor 2). Tmax data are shown in Table 4 together with dissolution percentage at 60 min. Full bioavailability profiles for EPA succinated capsules and AMR101 capsules are shown in FIGS. 2 and 3, respectively.

TABLE 4

Dissolution and Tmax.

| | Dissolution at 60 min (%) | $T_{max}$ (hrs) |
|---|---|---|
| Comparitor 1[1] | 77 | 6 |
| Comparitor 2[2] | 75 | 6 |
| AMR101[3] | 87 | 5 |

[1]Capsule shell = 220 mg; contents = 323 mg.
[2]Capsule shell = 134 mg; contents = 327 mg.
[3]Mean of three batches using RDC and pH 1.2.

As can be seen from Table 4, AMR101 exhibited greater E-EPA dissolution by 60 minutes, and had a shorter $T_{max}$ than was reported for Epadel present in succinated gelatin capsules.

We claim:

1. A method of reducing triglycerides comprising, identifying a group of subjects having a median triglyceride level of at least 500 mg/dl and orally administering daily to at least one subject in the group of subjects about 2500 mg to about 5000 mg of ethyl eicosapentaenoate, present in one or more capsules, wherein upon 12 weeks of said administering the at least one subject exhibits a reduction in triglycerides of at least about 15% without an increase of LDL-C of more than 5%.

2. The method of claim 1, wherein the group of subjects has a median fasting baseline LDL-C from about 50 mg/dl to about 300 mg/dl.

3. The method of claim 1, wherein the group of subjects has one or more of: a median baseline fasting non-HDL-C of about 200 mg/dl to about 300 mg/dl, a median baseline fasting total cholesterol of about 250 mg/dl to about 300 mg/dl, a median baseline fasting VLDL-C of about 140 mg/dl to about 200 mg/dl, and/or a median baseline fasting HDL-C of about 10 mg/dl to about 80 mg/dl.

4. The method of claim 1, wherein 12 weeks of said administering is effective to reduce triglycerides by at least about 30% without increasing LDL-C in the at least one subject.

5. The method of claim 1, wherein 12 weeks of said administering is effective to reduce apolipoprotein B in the at least one subject.

6. The method of claim 1, wherein 12 weeks of said administering is effective to reduce VLDL-C in the at least one subject.

7. The method of claim 1, wherein the group of subjects has a median fasting baseline triglyceride level of 500 mg/dl to 1500 mg/dl.

8. The method of claim 1, wherein the ethyl eicosapentaenoate is present in one or more dosage units.

9. The method of claim 8, wherein the dosage units are capsules.

10. A method of reducing triglycerides comprising, identifying a group of subjects having a median triglyceride level of at least 500 mg/dl and orally administering daily to at least one subject in the group 4 capsules, each capsule comprising about 900 mg to about 1 g of ethyl eicosapentaenoate, wherein upon 12 weeks of said administering the at least one subject exhibits a reduction in triglycerides by at least 15% without an increase of LDL-C of more than 5%.

11. The method of claim 10, wherein the group of subjects has a median fasting baseline LDL-C from about 50 mg/dl to about 300 mg/dl.

12. The method of claim 10, wherein the group of subjects has one or more of: a median baseline fasting non-HDL-C of about 200 mg/dl to about 300 mg/dl, a median baseline fasting total cholesterol of about 250 mg/dl to about 300 mg/dl, a median baseline fasting VLDL-C of about 140 mg/dl to about 200 mg/dl, and/or a median baseline fasting HDL-C of about 10 mg/dl to about 80 mg/dl.

13. The method of claim 10, wherein 12 weeks of said administering is effective to reduce triglycerides by at least about 30% without increasing LDL-C in the at least one subject.

14. The method of claim 10, wherein 12 weeks of said administering is effective to reduce apolipoprotein B in the at least one subject.

15. The method of claim 10, wherein 12 weeks of said administering is effective to reduce VLDL-C in the at least one subject.

16. The method of claim 10, wherein the group of subjects has a median fasting baseline triglyceride level of 500 mg/dl to 1500 mg/dl.

17. A method of reducing triglycerides comprising, identifying a group of subjects having a median triglyceride level of at least 500 mg/dl, orally administering daily to at least one subject in the group about 4 g of fatty acids, at least about 90% by weight of which are ethyl eicosapentaenoate, wherein upon 12 weeks of said administering the at least one subject exhibits a reduction in triglycerides by at least 15% without an increase of LDL-C of more than 5%.

18. The method of claim 17, wherein the group of subjects has a median fasting baseline LDL-C from about 50 mg/dl to about 300 mg/dl.

19. The method of claim 17, wherein the group of subjects has one or more of: a median baseline fasting non-HDL-C of about 200 mg/dl to about 300 mg/dl, a median baseline fasting total cholesterol of about 250 mg/dl to about 300 mg/dl, a median baseline fasting VLDL-C of about 140 mg/dl to about 200 mg/dl, and/or a median baseline fasting HDL-C of about 10 mg/dl to about 80 mg/dl.

20. The method of claim 17, wherein 12 weeks of said administering is effective to reduce triglycerides by at least about 30% without increasing LDL-C in the at least one subject.

21. The method of claim 17, wherein 12 weeks of said administering is effective to reduce apolipoprotein B in the at least one subject.

22. The method of claim 17, wherein 12 weeks of said administering is effective to reduce VLDL-C in the at least one subject.

23. The method of claim 17, wherein the group of subjects has a median fasting baseline triglyceride level of 500 mg/dl to 1500 mg/dl.

24. The method of claim 17, wherein the fatty acids other than ethyl eicosapentaenoate comprise at least one fatty acid selected from the group consisting of linolenic acid, ethyl linolenic acid, arachidonic acid, ethyl arachidonic acid, stearadonic acid, ethyl stearadonic acid, eicosatrienoic acid, ethyl eicosatrienoic acid, docosapentaenoic acid, and ethyl docosapentaenoic acid.

25. The method of claim 17, wherein the fatty acids are present in one or more dosage units.

26. The method of claim 25, wherein the dosage units are capsules.

\* \* \* \* \*